(12) United States Patent
Lahmann et al.

(10) Patent No.: US 11,672,898 B2
(45) Date of Patent: Jun. 13, 2023

(54) MICROFLUIDIC REMOVAL OF EXCESS BILIRUBIN FROM BLOOD

(71) Applicant: Oregon State University, Corvallis, OR (US)

(72) Inventors: John Lahmann, Corvallis, OR (US); Adam Z. Higgins, Corvallis, OR (US)

(73) Assignee: OREGON STATE UNIVERSITY, Corvallis, OR (US)

( * ) Notice: Subject to any disclaimer, the term of this patent is extended or adjusted under 35 U.S.C. 154(b) by 1012 days.

(21) Appl. No.: 16/431,928

(22) Filed: Jun. 5, 2019

(65) Prior Publication Data

US 2019/0374701 A1 Dec. 12, 2019

Related U.S. Application Data

(60) Provisional application No. 62/682,431, filed on Jun. 8, 2018.

(51) Int. Cl.
*A61M 1/36* (2006.01)
*A61M 60/104* (2021.01)
*A61M 60/109* (2021.01)

(52) U.S. Cl.
CPC ............ *A61M 1/3672* (2013.01); *A61M 1/36* (2013.01); *A61M 1/3623* (2022.05); *A61B 2503/045* (2013.01); *A61M 60/104* (2021.01); *A61M 60/109* (2021.01); *A61M 2205/0244* (2013.01)

(58) Field of Classification Search
CPC .... A61M 1/3681; A61M 1/3672; A61M 1/36; A61M 1/3623; A61M 60/104; A61M 60/109; A61M 2205/0244; A61M 2205/12; A61M 2205/3606; A61M 2205/366; A61B 2503/045; G01N 2800/085

See application file for complete search history.

(56) References Cited

U.S. PATENT DOCUMENTS

| 4,456,512 A | 6/1984 | Bieler et al. |
| 5,254,249 A | 10/1993 | Terada et al. |
| 5,433,738 A * | 7/1995 | Stinson .................... A61L 2/10 |
| | | 250/435 |

(Continued)

OTHER PUBLICATIONS

Onishi, Shoju, Susumu Itoh, and Kenichi Isobe. "Wavelength-dependence ... photochemical changes from (ZZ)-bilirubin IX α to (EZ)-cyclobilirubin IX α via (EZ)-bilirubin." Biochemical journal 236.1 (1986): 23-29. (Year: 1986).*

(Continued)

*Primary Examiner* — Adam Marcetich
(74) *Attorney, Agent, or Firm* — Schwabe, Williamson & Wyatt, P.C.

(57) ABSTRACT

A microfluidic photoreactor for treating excess bilirubin in blood, having: a microfluidic channel module; an illumination module comprising one or more illumination sources disposed about the microfluidic channel module and configured to illuminate blood passing through at least one microfluidic channel of the microfluidic channel module; and a heat exchanger module coupled to the at least one microfluidic channel module, wherein the heat exchanger module is configured to extract heat from the at least one (Continued)

microfluidic channel. A system including a microfluidic photoreactor and a method of treating excess bilirubin in blood.

24 Claims, 10 Drawing Sheets

(56) References Cited

U.S. PATENT DOCUMENTS

| | | | |
|---|---|---|---|
| 5,702,432 | A | 12/1997 | Chen et al. |
| 6,464,936 | B1* | 10/2002 | Mowat .................. A61L 2/0011 250/455.11 |
| 7,955,504 | B1* | 6/2011 | Jovanovic ............ B01D 63/088 210/321.71 |
| 9,265,876 | B1* | 2/2016 | Ben-Hur ................ G01K 13/02 |
| 2004/0061079 | A1* | 4/2004 | Thompson .............. C03C 25/12 250/492.22 |
| 2004/0186410 | A1* | 9/2004 | Davidner ............ A61M 1/3683 424/140.1 |
| 2005/0015040 | A1* | 1/2005 | Wuepper ............. A61M 1/3681 604/5.01 |
| 2005/0152146 | A1* | 7/2005 | Owen .................... H05B 47/10 362/294 |
| 2007/0155006 | A1 | 7/2007 | Levin |
| 2007/0262020 | A1* | 11/2007 | Wang ...................... A61M 1/16 210/243 |
| 2009/0131771 | A1* | 5/2009 | Takeda ................ A61M 1/3681 600/315 |
| 2011/0021966 | A1* | 1/2011 | Leonard .............. A61M 1/3681 210/748.14 |
| 2013/0234039 | A1* | 9/2013 | Bontinck .............. A61L 2/0058 250/435 |
| 2013/0345614 | A1* | 12/2013 | Mane ..................... G01N 33/70 422/44 |
| 2017/0252701 | A1* | 9/2017 | Nosrati ............... A61M 1/1601 |

OTHER PUBLICATIONS

Gutcher, Gary R., William M. Yen, and Gerard B. Odell. "The in vitro and in vivo photoreactivity of bilirubin: I. Laser-defined wavelength dependence." Pediatric Research 17.2 (1983): 120-123. (Year: 1983).*

Enwemeka CS. Antimicrobial blue light: an emerging alternative to antibiotics. Photomed Laser Surg. 2013;31 (11):509-11.

Bumah VV, Masson-meyers DS, Cashin SE, Enwemeka CS. Wavelength and bacterial density influence the bactericidal effect of blue light on methicillin-resistant *Staphylococcus aureus* (MRSA). Photomed Laser Surg. 2013;31 (11):547-53.

Enwemeka CS, Williams D, Enwemeka SK, Hollosi S, Yens D. Blue 470-nm light kills methicillin-resistant *Staphylococcus aureus* (MRSA) in vitro. Photomed Laser Surg. 2009;27(2):221-6.

Enwemeka CS, Williams D, Hollosi S, Yens D, Enwemeka SK. Visible 405 nm SLD light photo-destroys methicillin-resistant *Staphylococcus aureus* (MRSA) in vitro. Lasers Surg Med. 2008;40(10):734-7.

Thompson BL, Wyckoff SL, Haverstick DM, Landers JP. Simple, Reagentless Quantification of Total Bilirubin in Blood Via Microfluidic Phototreament and Image Analysis. 2017 American Chemical Society. Anal. Chem. 2017, 89, 3228-3234.

* cited by examiner

MICROFLUIDIC REMOVAL OF EXCESS BILIRUBIN FROM BLOOD

CROSS-REFERENCE TO RELATED APPLICATION

This application claims the priority benefit of the earlier filing date of U.S. Provisional Application No. 62/682,431, which is hereby incorporated herein by reference in its entirety.

FIELD OF THE DISCLOSURE

The present disclosure relates the treatment of blood disorders, and, in particular, the extracorporeal treatment of excess levels of bilirubin in the blood.

BACKGROUND

Over half of newborns develop jaundice, a condition caused by high levels of bilirubin in the blood. As a percentage, this is even more pronounced in premature births. Bilirubin is neurotoxic and its accumulation in the brain can lead to devastating consequences including seizures, brain damage and death. The frontline treatment for jaundice is phototherapy, which involves illumination of the infant with blue light to catalyze conversion of bilirubin to nontoxic isomers that are then excreted in bile and urine. Phototherapy is a slow process, often requiring days to reduce the bilirubin concentration to safe levels. In cases when phototherapy fails to prevent dangerous bilirubin levels, a double volume exchange transfusion is used to replace the baby's blood with donor blood. Exchange transfusions introduce serious complications, including a mortality rate of ~1% and significant morbidity in about 10% of cases. In the US there are about 30,000 cases per year of jaundice rated as severe, extreme or hazardous, indicating high risk for brain damage and meeting the criteria for exchange transfusion. The number of cases worldwide exceeds 1 million. Thus, there is a critical need for a new treatment strategy that rapidly reduces bilirubin levels without introducing high risk of mortality and morbidity. Moreover, even newborns with intermediate bilirubin levels develop brain damage in some cases. These newborns are currently treated with phototherapy. A safe method for rapidly reducing bilirubin levels would lower the risk of brain damage for these infants, and reduce disruptions to parental bonding commonly associated with prolonged phototherapy. Thus, there is a significant need for new technologies that enable rapid and safe treatment of jaundice.

DETAILED DESCRIPTION

Figure 1A:
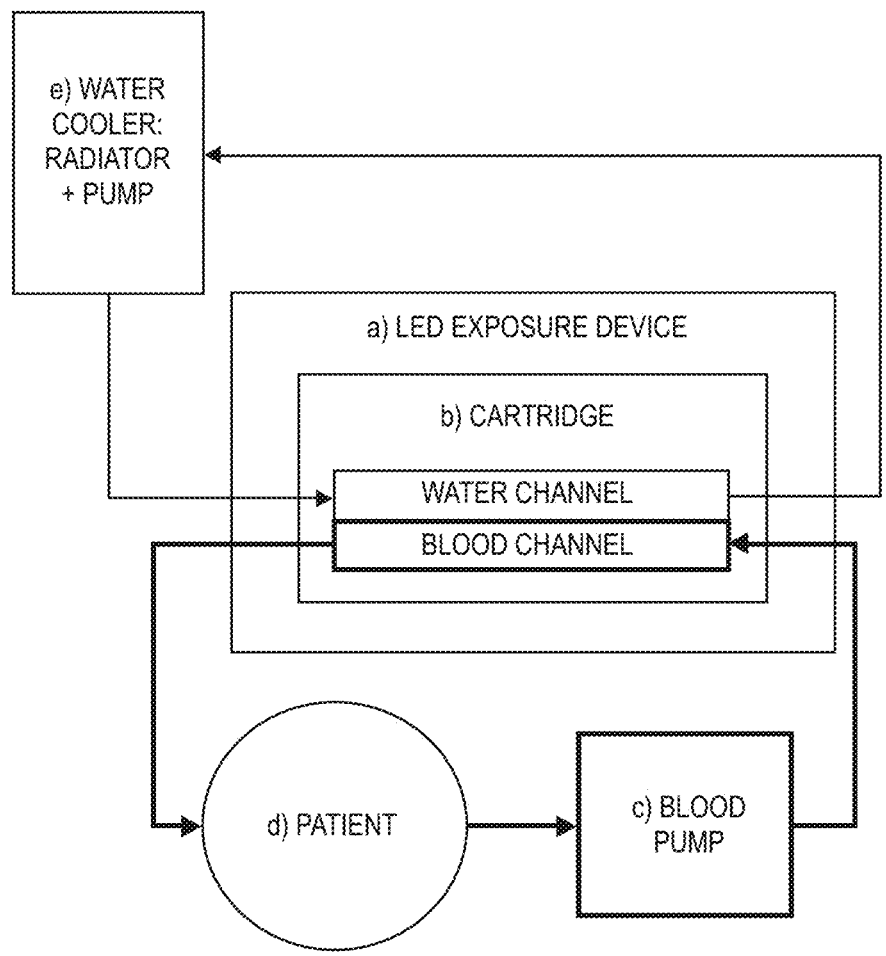
FIGS. 1A-1B are a schematic and a digital image illustrating an exemplary design for treatment of a subject in accordance with embodiments herein. The LED exposure device (a) includes of a top and bottom array of LED lights. A disposable treatment cartridge (b) is suspended between the array so that light enters from both sides. The treatment cartridge has two channels, one for the blood to pass through and one for the water (or other coolant). The channels is separated by a transparent layer that is impermeable to the fluids. Blood is pumped through the device by the blood pump (c), from the patient (d), through the blood channel, and is returned to the patient via catheters and tubing. The water cooler (e) pumps water (or coolant) through the cartridge's water channel and returns it to the cooling device. The water is cooled either by radiators or a refrigeration system.

In the following detailed description, reference is made to the accompanying drawings which form a part hereof, and in which are shown by way of illustration embodiments that may be practiced. It is to be understood that other embodiments may be utilized and structural or logical changes may be made without departing from the scope. Therefore, the following detailed description is not to be taken in a limiting sense, and the scope of embodiments is defined by the appended claims and their equivalents.

Various operations may be described as multiple discrete operations in turn, in a manner that may be helpful in understanding embodiments; however, the order of description should not be construed to imply that these operations are order dependent.

The terms "coupled" and "connected," along with their derivatives, may be used. It should be understood that these terms are not intended as synonyms for each other. Rather, in particular embodiments, "connected" may be used to indicate that two or more elements are in direct physical contact with each other. "Coupled" may mean that two or more elements are in direct physical contact. However, "coupled" may also mean that two or more elements are not in direct contact with each other, but yet still cooperate or interact with each other.

For the purposes of the description, a phrase in the form "A/B" or in the form "A and/or B" means (A), (B), or (A and B). For the purposes of the description, a phrase in the form "at least one of A, B, and C" means (A), (B), (C), (A and B), (A and C), (B and C), or (A, B and C). For the purposes of the description, a phrase in the form "(A)B" means (B) or (AB) that is, A is an optional element.

The description may use the terms "embodiment" or "embodiments," which may each refer to one or more of the same or different embodiments. Furthermore, the terms "comprising," "including," "having," and the like, as used with respect to embodiments, are synonymous, and are generally intended as "open" terms (e.g., the term "including" should be interpreted as "including but not limited to," the term "having" should be interpreted as "having at least," the term "includes" should be interpreted as "includes but is not limited to," etc.).

With respect to the use of any plural and/or singular terms herein, those having skill in the art can translate from the plural to the singular and/or from the singular to the plural as is appropriate to the context and/or application. The various singular/plural permutations may be expressly set forth herein for sake of clarity.

Unless otherwise noted, technical terms are used according to conventional usage. Definitions of common terms in molecular biology can be found in Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); and Robert A. Meyers (ed.), Molecular Biology and Biotechnology: a Comprehensive Desk Reference, published by VCH Publishers, Inc., 1995 (ISBN 9780471185710); and other similar references.

The term subject includes multi-cellular vertebrate organisms, a category that includes, for example, mammals. The term mammal includes both human and non-human mammals. Similarly, the term "subject" includes both human and veterinary or laboratory subjects, for example, humans, non-human primates, mice, rats, dogs, cats, horses, and cows.

INTRODUCTION

Hyperbilirubinemia affects approximately 60 percent of newborns (Maisels M J, McDonagh A F. Phototherapy for neonatal jaundice. N. Engl. J. Med. February 2008; 358(9): 920-928). Bilirubin is neurotoxic and can lead to bilirubin encephalopathy, with symptoms of motor function disorders, auditory dysfunction, seizures, and death (Shapiro S M. Bilirubin toxicity in the developing nervous system. Pediatr. Neurol. November 2003; 29(5):410-421). Current treatment for hyperbilirubinemia involves the use of whole body phototherapy in which bilirubin undergoes photoreaction to conformational and structural isomers that are more readily excreted from the body (Agati G, Fusi F, Donzelli G P, Pratesi R. Quantum yield and skin filtering effects on the formation rate of lumirubin. J. Photochem. Photobiol. B. May 1993; 18(2-3):197-20). This treatment is sufficient in most cases of mild hyperbilirubinemia and is currently the best practice in terms of safety and simplicity. More severe cases that do not respond to phototherapy require exchange transfusion, a relatively risky procedure in which the infant's bilirubin-rich blood is replaced with donor blood in small increments (Center TNEMCE-bP. AHRQ Evidence Report/Technology Assessment No. 65, Management of Neonatal Hyperbilirubinemia. AHRQ. 2002). In addition, children and adults can also suffer from hyperbilirubinemia as a result of liver failure or genetic diseases such as Crigler-Najjar syndrome. Because these individuals are much larger than newborn babies, conventional phototherapy is ineffective. Exchange transfusion is the only option for effectively reducing bilirubin levels and liver transplantation is the only long-term cure. Individuals with type I Crigler-Najjar syndrome require lifelong treatment to reduce bilirubin levels, and even with treatment these individuals typically only live to age 30. Crigler-Najjar syndrome affects about 10,000 people worldwide. Thus, there is a need for a safer alternative to exchange transfusion that can be quickly administered when there is potential for brain injury related to high bilirubin levels. In addition, exchange transfusion cannot always be initiated in smaller medical facilities; an alternative could be extremely valuable to these communities.

The present disclosure seeks to change the current paradigm for treatment of hyperbilirubinemia and in particular neonatal hyperbilirubinemia by offering a safe and convenient option to rapidly reduce serum bilirubin levels. Although phototherapy is sufficient in many cases for managing bilirubin levels, this treatment approach is limited because light can only penetrate a small layer at the surface and the majority of the energy carried by the light is converted to heat. This heat deposition limits the light intensity that can safely be used (Lamola A A, Bhutani V K, Wong R J, Stevenson D K, McDonagh A F. The effect of hematocrit on the efficacy of phototherapy for neonatal jaundice. Pediatr. Res. July 2013; 74(1):54-60; Lamola A A. A Pharmacologic View of Phototherapy. Clin. Perinatol. June 2016; 43(2):259-276). As a result, phototherapy typically reduces serum bilirubin levels slowly and often requires treatment over a period of days. Currently, the only option for more quickly reducing serum bilirubin levels is exchange transfusion, a procedure associated with significant complications including coagulopathy, necrotizing enterocolitis and increased risk of infection (Schreuder A B, Vanikova J, Vitek L, et al. Optimizing exchange transfusion for severe unconjugated hyperbilirubinemia: studies in the Gunn rat. PLoS ONE. 2013; 8(10):e77179). In an attempt to develop alternatives to exchange transfusion, several groups have investigated the use of extracorporeal circuits for removal of bilirubin from blood (Altintas E B, Turkmen D, Karakoc V, Denizli A. Efficient Removal of Bilirubin from Human Serum by Monosize Dye Affinity Beads. J Biomat Sci-Polym E. 2011; 22(7):957-971; Avramescu M E, Sager W F C, Borneman Z, Wessling M. Adsorptive membranes for bilirubin removal. J Chromatogr B. Apr. 25 2004; 803(2):215-223; Scharschmidt B F, Plotz P H, Berk P D, Waggoner J G, Vergalla J. Removing substances from blood by affinity chromatography. II. Removing bilirubin from the blood of jaundiced rats by hemoperfusion over albumin-conjugated agarose beads. J. Clin. Invest. March 1974; 53(3):786-795; Mullon C J P, Tosone C M, Langer R.

Simulation of Bilirubin Detoxification in the Newborn Using an Extracorporeal Bilirubin Oxidase Reactor. Pediatr. Res. November 1989; 26(5):452-457; Sideman S, Mor L, Mordohovich D, Mihich M, Zinder O, Brandes J M. Invivo Hemoperfusion Studies of Unconjugated Bilirubin Removal by Ion-Exchange Resin. T Am Soc Art Int Org. 1981; 27:434-438). However, these previous devices suffer from key deficiencies that have hindered their clinical acceptance, including high device priming volume, the requirement for fast flow rates, and poor biocompatibility. Large internal volumes require pre-priming with donor blood, one of the primary issues of exchange transfusion the disclosed methods, systems, and devices avoid. Fast flow rates typically require access to vasculature via central venous catheter which requires specialized medical personnel to place and monitor.

To overcome the problem outlined above the inventors have developed microfluidic photoreaction based devices, systems, and methods to treat elevated bilirubin levels in a neonate. As demonstrated by the working Examples presented herein the inventers have overcome the above problems by leveraging microscale technology to enable rapid photoconversion of bilirubin using a small device (~5-20 mL internal volume) and low flow rate (1-8 mL/min). This device can also be expanded to treat elevated bilirubin levels in a larger subject, such as a normal infant, child, and/or adult subject, for example by increasing the volume and/or flor rate of the device.

Aspects of the present disclosure are directed to devices, systems, and methods for the microfluidic photoreaction of extracorporeal blood treatment to reduce bilirubin level, for example by converting the bilirubin to isomers that are more easily removed from the body. As disclosed herein one of the key advantage of the device is that the microfluidic length scale overcomes challenges associated with light attenuation, allowing illumination of the entire blood volume passing through the device. As shown in the Examples below, working embodiments of the device demonstrate that the device enables bilirubin levels to be reduced as quickly as exchange transfusion, while also maintaining a small device volume and low blood flow rate for improved safety. This technology has the potential to significantly improve neonatal care.

In the US alone approximately 30,000 newborns per year suffer from hyperbilirubinemia rated as severe, extreme or hazardous, (Christensen R D, Lambert D K, Henry E, et al. Unexplained extreme hyperbilirubinemia among neonates in a multihospital healthcare system. Blood Cells Mol. Dis. February 2013; 50(2):105-109; Bhutani V K, Stevenson D K. The Need for Technologies to Prevent Bilirubin-Induced Neurologic Dysfunction Syndrome. Semin. Perinatol. June 2011; 35(3):97-100) and the number of cases exceeds 1 million per year worldwide. All of these newborns would benefit from the disclosed technology. More rapid reduction of bilirubin levels could also benefit neonates with less severe hyperbilirubinemia. Recent evidence indicates that prolonged exposure to intermediate bilirubin levels can cause long-term complications associated with damage to the central nervous system (Sugama S, Soeda A, Eto Y. Magnetic resonance imaging in three children with kernicterus. Pediatr. Neurol. October 2001; 25(4):328-331). These newborns are currently treated with phototherapy, which slowly reduces bilirubin levels, often over several days of treatment. A safer alternative to exchange transfusion which rapidly reduces bilirubin levels would reduce the risk of neurological complications for these newborns (Watchko J F, Maisels M J. The enigma of low bilirubin kernicterus in premature infants: Why does it still occur, and is it preventable? Semin. Perinatol. November 2014; 38(7):397-406). Moreover, bleeding complications associated with systemic anticoagulation are a common problem with extracorporeal circuits, particularly in the neonatal population. For instance, over 10% of newborns treated with extracorporeal membrane oxygenation experience intracranial hemorrhage, often with devastating consequences (Polito A, Barrett C S, Wypij D, et al. Neurologic complications in neonates supported with extracorporeal membrane oxygenation. An analysis of ELSO registry data. Intensive Care Med. September 2013; 39(9):1594-1601). In this regard, the heparin-based surface coating proposed here is broadly applicable to medical device surfaces and has the potential to eliminate the need for systemic anticoagulation in extracorporeal circuits. These surface coatings could also reduce complications associated with coagulation on the surface of blood-contacting medical devices such as intravenous catheters.

Microfluidic Photoreactor

Aspects of the present disclosure are drawn to a microfluidic photoreactor (which can be referred to herein as the "microfluidic device" or "device") that is used to convert bilirubin in the blood of a subject to products that can be physiologically eliminated by the subject, for example excreted in the bile or urine. In embodiments, a microfluidic photoreactor for treating excess bilirubin in blood includes a microfluidic channel module, an illumination module, and a heat exchanger module.

In embodiments, the microfluidic channel module includes at least one microfluidic channel. In embodiments, the microfluidic channel has: a first end; a second end; a channel height; a channel width; and a channel length. The first end of the microfluidic channel includes a sample inlet port that is configured for blood to enter the microfluidic channel. The second end of the microfluidic channel includes a sample exit port for blood to exit the microfluidic channel and be returned to the subject. The microfluidic channel module is configured to pass blood from the sample inlet port to the sample exit port, for example, through the at least one microfluidic channel. Typically, a single microfluidic channel is preferred; however, this does not exclude devices having multiple, such as 1, 2, 3, 4, or more microfluidic channels. Multichannel device can have 2 or more microfluidic channels in parallel. Device safely may be further improved by coating the blood contacting surfaces in the extracorporeal circuit with an anti-fouling and/or anti-coagulant layer. Thus, in embodiments, the surfaces of the at least one microfluidic channel module that contact blood are coated with an anticoagulant and/or antifouling agent. In certain embodiments, the blood contacting surfaces of a disclosed microfluidic photoreactor are coated using a polyethylene oxide (PEO) brush layer, with heparin tethered in a highly-active "end-on" fashion at the PEO chain ends. In certain embodiments, the blood contacting surfaces of a disclosed microfluidic photoreactor are coated using a heparin conjugated to a coating comprised of polydopamine. Polydopamine coatings have previously been shown to form readily on a variety of surfaces including the plastics commonly used in extracorporeal circuits. Studies disclosed herein demonstrate protein-repellent characteristics and strong anticoagulant function of the coating, highlighting the potential for operation of the extracorporeal circuit without systemic anticoagulants. This represents a significant advantage as neonates are particularly susceptible to complications associated with the use of systemic anticoagulants, for example, neonates are prone to intracranial hemorrhage. In embodiments, the one or more microfluidic channels are preloaded with a biologically compatible fluid (such as saline, or other isotonic solution), so that there is little to no dead volume when the device is fluidly connected to a subject. Typically, the materials for construction of the one or more microfluidic channels are chosen such that light with a wavelength of between about 400 nm and 520 nm can pass though the walls, i.e. top and bottom of the channel and allow the blood to become illuminated, for example a transparent (visible light range), biocompatible material. In embodiments, the one or more microfluidic channels are fabricated from plastic or glass, such as PMMA (acrylic) or polycarbonate.

In embodiments, the illumination module includes one or more illumination sources that are disposed about the microfluidic channel module and configured to illuminate blood passing through the at least one microfluidic channel. The height of the at least one microfluidic channel is selected such that the illumination sources are able to illuminate, to a high percentage, the blood passing through the at least one microfluidic channel. As is detailed in the Examples below, there is a tradeoff between the height of the channel and the amount of light energy needed to penetrate and thus illuminate blood, i.e. the bigger the height of the channel the more light intensity is needed to fully penetrate the blood. However, if the intensity of the light too high, then damage to cells, such as the DNA of white blood cells, can occur. Thus, the channel height may be selected based on the flow rate of the blood, the intensity of the light, and the wavelength used among others. In embodiments, the channel height is between about 50 µm and about 500 µm, such as about 50 µm, 75 µm, 100 µm, 125 µm, 150 µm, 175 µm, 200 µm, 225 µm, 250 µm, 275 µm, 300 µm, 325 µm, 350 µm, 375 µm, 400 µm, 425 µm, 450 µm, 475 µm, or 500 µm. The width and the length of the microfluidic channel are selected such that the volume of blood in the microfluidic photoreactor remains low, which is important for neonates undergoing therapy for elevated bilirubin levels. For neonates, about 5 mL to about 10 mL would be desired. However, for larger subjects, such as adults and children, larger volumes me be desired, for example up to about 100 mL or even larger. Thus, in embodiments, the at least one microfluidic channel has an internal volume, and the internal volume is selected to be between about 5 mL and about 100 mL, such as about 5 mL, 6 mL, 7 mL, 8 mL, 9 mL, 10 mL, 11 mL, 12 mL, 13 mL, 14 mL, 15 mL, 16 mL, 17, mL 18 mL, 19 mL, 20 mL, 21 mL, 22 mL, 23 mL, 24 mL, 25 mL, 26 mL, 27, mL 28 mL, 29 mL, 30 mL, 31 mL, 32 mL, 33 mL, 34 mL, 35 mL, 36 mL, 37, mL 38 mL, 39 mL, 40 mL, 41 mL, 42 mL, 43 mL, 44 mL, 45 mL, 46 mL, 47, mL 48 mL, 49 mL, 50 mL, 51 mL, 52 mL, 53 mL, 54 mL, 55 mL, 56 mL, 57, mL 58 mL, 59 mL, 60 mL, 61 mL, 62 mL, 63 mL, 64 mL, 65 mL, 66 mL, 67, mL 68 mL, 69 mL, 70 mL, 71 mL, 72 mL, 73 mL, 74 mL, 75 mL, 76 mL, 77, mL 78 mL, 79 mL, 80 mL, 81 mL, 82 mL, 83 mL, 84 mL, 85 mL, 86 mL, 87, mL 88 mL, 89 mL, 90 mL, 91 mL, 92 mL, 93 mL, 94 mL, 95 mL, 96 mL, 97, mL 98 mL, 99 mL, or 100 mL. For noenates, the flow rates would typically be lower than adults, for example to account for fragility of the neonate and the lower total blood volume that needs to be treated. For a neonate, a flow rate of about 1 mL/min to about 10 mL/min may be beneficial. However, adults and/or children may be able to tolerate a higher flow rate, such as between about 20 mL/min to about 200 mL/min. Thus, in embodiments, the photoreactor has a flow rate of between about 1 mL/min and about 200 mL/min, such as about 1 mL/min, 2 mL/min, 3 mL/min, 4 mL/min, 5 mL/min, 6 mL/min, 7 mL/min, 8 mL/min, 9 mL/min, 10 mL/min, 15 mL/min, 20 mL/min, 25 mL/min, 30 mL/min, 35 mL/min, 40 mL/min, 45 mL/min, 50 mL/min, 60 mL/min, 70 mL/min, 80 mL/min, 90 mL/min, 100 mL/min, 125 mL/min, 150 mL/min, 175 mL/min, or 200 mL/min. In embodiments, the channel length is typically selected between about 10 cm and about 100 cm although longer and shorter length are contemplated. In embodiments, the channel width is between about 1 cm and about 4 cm, however, wider and narrower channels are contemplated as are parallel configurations with multiple parallel channels (typically of substantially similar width). In embodiments, multiple parallel channels may be used in the scaled up device, for example so that the walls at the top and bottom of the microfluidic channel do not deform, either by internal pressure or sagging.

In embodiments, the illumination module includes one or more illumination sources. In embodiments, the one or more illumination sources comprise a first set of illumination sources, such as an array, configured to illuminate a top side of the at least one microfluidic channel and second set of set illumination sources, such as an array, configured to illuminate a bottom side of the microfluidic channel. By illuminating both the top and bottom of the microfluidic channel efficiency is increased over a device where only one side is illuminated. For example, you can use a microfluidic channel with a height twice that of a microfluidic channel where only a single side is illuminated. In embodiments, the one or more illumination sources emit light with a wavelength between about 415 nm and about 520 nm, such as about 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, and 520 nm. In embodiments, the one or more illumination sources emit light with a light intensity between about 25 $mW/cm^2$ and about 500 $mW/cm^2$ for each exposure surface, for example each side of microfluidic channel, such as about 25 $mW/cm^2$, 50 $mW/cm^2$, 75 $mW/cm^2$, 100 $mW/cm^2$, 125 $mW/cm^2$, 150 $mW/cm^2$, 175 $mW/cm^2$, 200 $mW/cm^2$, 225 $mW/cm^2$, 250 $mW/cm^2$, 275 $mW/cm^2$, 300 $mW/cm^2$, 225 $mW/cm^2$, 250 $mW/cm^2$, 375 $mW/cm^2$, 400 $mW/cm^2$, 425 $mW/cm^2$, 450 $mW/cm^2$, 475 $mW/cm^2$, or 500 $mW/cm^2$. By way of example, if a microfluidic channel were elluminated on both sides (top and bottom) with an illumination source, each of those sides would be exposed to a light intensity between about 25 $mW/cm^2$ and about 500 $mW/cm^2$. In embodiments, the one or more illumination sources comprise LEDs. In embodiments, the LEDs comprises LED arrays.

As disclosed herein the microfluidic photoreactor includes a heat exchanger module is coupled to the at least one microfluidic channel module. The heat exchanger module is configured to extract heat from the at least one microfluidic channel and thus keep the blood in the at least one microfluidic channel from overheating. In embodiments, the heat exchanger module comprises a cooling channel having a first end and a second end, wherein the first end comprises a cooling fluid inlet port and the second end comprises a cooling fluid exit port, and where the heat exchanger module is configured to flow cooled cooling fluid. As cooling liquid is passed through the cooling channel any excess heat is extracted from the one or more microfluidic channels. In embodiments, the cooling channel is directly coupled to the walls of the microfluidic channel, for example, only a single wall of the microfluidic channel may separate the microfluidic channel form the cooling channel. Such direct contact would greatly facilitate heat transfer from the blood in the one or more microfluidic channels to the cooling liquid in the cooling channel. In some embodiments, there is a cooling channel on both the top and bottom of the one or more microfluidic channels, for example between the illumination sources and the one or more microfluidic channels. I other embodiments, the cooling fluid is directed around housings for the illumination sources such that the light from the illumination sources does not need to travel through the cooling fluid to read the one or more microfluidic channels and blood.

In embodiments, the microfluidic channel is housed within a cassette, such as a single use and/or disposable cassette, that reversibly couples to the illumination module such that it can be removed and/or replaces with a new cassette for each subject. In embodiments, the illumination module is housed within a housing, that in some embodiments is configured to allow the cassette to couple thereto. In embodiments, the cassette further comprises the heat exchanger module. In embodiments, the microfluidic photoreactor includes cooling fluid, such as water, ethylene glycol, or other fluid, in the cooling channel.

Systems

Aspects of the disclosure are drawn to a system for treating excess bilirubin in blood. In embodiments, the system includes a microfluidic photoreactor as described herein and a pump in fluid communication with the at least one microfluidic channel, wherein the pump is configured to pump blood from a subject through the one or more channels of the microfluidic photoreactor. Various pumps are known the art that are compatible with blood pumping. In embodiments, the pump comprises a peristaltic pump. In embodiments, the pump is configured to pump blood at a flow rate of between about 1 mL/min and about 200 mL/min, such as about such as about 1 mL/min, 2 mL/min, 3 mL/min, 4 mL/min, 5 mL/min, 6 mL/min, 7 mL/min, 8 mL/min, 9 mL/min, 10 mL/min, 15 mL/min, 20 mL/min, 25 mL/min, 30 mL/min, 35 mL/min, 40 mL/min, 45 mL/min, 50 mL/min, 60 mL/min, 70 mL/min, 80 mL/min, 90 mL/min, 100 mL/min, 125 mL/min, 150 mL/min, 175 mL/min, or 200 mL/min. In embodiments, the system further includes a cooling unit in fluid communication with the heat exchanger module, where the cooling unit is configured to cool the cooling fluid passing though the heat exchanger module. In certain embodiments, the cooling unit is configured to maintain the blood at a physiologic temperature, such as 37° C. for a human subject. In embodiments, the cooling unit comprises a radiator and/or a chiller. In embodiments, system includes a coolant pump the pumps the cooling fluid through the cooling channel. In embodiments, the system is an extracorporeal circuit. The system can include several discrete components that are connected together or can be contained in a single device or housing. In some embodiments, the system allows for a cartridge, such as a single use cartridge containing the one or more microfluidic channels as described above, to be snapped or otherwise swapped in and out.

Methods of Treatment

Further aspects of the disclosure concern a method of treating excess bilirubin in blood. In embodiments, the method includes passing blood of a subject through the at least one microfluidic channel of the microfluidic photoreactor and/or system as described above to treat the blood and returning the treated blood to the subject. Thus, the method may include coupling the microfluidic photoreactor and/or system as described above to blood vessels of a subject and pumping the blood through the microfluidic photoreactor and/or system as described above before it is returned to the subject. In embodiments, the microfluidic photoreactor and/or system is directly connected to the vasculature, for example, as a standalone extracorporeal circuit. Alternatively, In embodiments, the microfluidic photoreactor and/or system added in series to an existing circuit, for example, extracorporeal membrane oxygenation (ECMO) is commonly used to augment the lung function of premature babies. This same patient population is likely to have hyperbilirubinemia and could benefit from treatment with the microfluidic photoreactor and/or system. The photoreactor design facilitates its use as an add-on to an existing extracorporeal circuit because: (1) the device has a small internal volume, (2) the device operates at low blood velocities. Together these features reduce the risk associated with bringing too much blood out of the body, as well as risk of damage to blood cells or coagulation induced by fluid shear. In embodiments, the blood of a subject is exposed to incident light in the microfluidic photoreactor and/or system as described above to convert the bilirubin to products that can be physiologically disposed of by the subject. These configurations could be used with an anticoagulant surface coating that can prevent coagulation without the need for systemic anticoagulants. The extracorporeal circuit could also be operated using systemic anticoagulants, such as the gold standard heparin, as well as new anticoagulants that are particularly promising for extracorporeal circuits such as antibodies targeting factor XI. In embodiments, the blood from the subject is exposed light with a wavelength between about 415 nm and about 520 nm, such as about 415 nm, 420 nm, 425 nm, 430 nm, 435 nm, 440 nm, 445 nm, 450 nm, 455 nm, 460 nm, 465 nm, 470 nm, 475 nm, 480 nm, 485 nm, 490 nm, 495 nm, 500 nm, 505 nm, 510 nm, 515 nm, and 520 nm. In embodiments, the blood from the subject is exposed to light with a light intensity between about 25 mW/cm$^2$ and about 500 mW/cm$^2$ for each exposure surface, for example each side of microfluidic channel, such as about 25 mW/cm$^2$, 50 mW/cm$^2$, 75 mW/cm$^2$, 100 mW/cm$^2$, 125 mW/cm$^2$, 150 mW/cm$^2$, 175 mW/cm$^2$, 200 mW/cm$^2$, 225 mW/cm$^2$, 250 mW/cm$^2$, 275 mW/cm$^2$, 300 mW/cm$^2$, 225 mW/cm$^2$, 250 mW/cm$^2$, 375 mW/cm$^2$, 400 mW/cm$^2$, 425 mW/cm$^2$, 450 mW/cm$^2$, 475 mW/cm$^2$, or 500 mW/cm$^2$. In embodiments, the subject is selected for treatment as diagnosed with excess bilirubin in the blood, for example having a bilirubin level above about 1.2 to 1.5 mg/dL. In embodiments, the subject is a neonate. In embodiments, the subject is an adult or child, for example an adult or child suffering from jaundice, liver failure, Crigler-Najjar syndrome, and/or Gilbert's syndrome.

EXAMPLES

Example 1

Exemplary Microfluidic Device

Figure 6A:
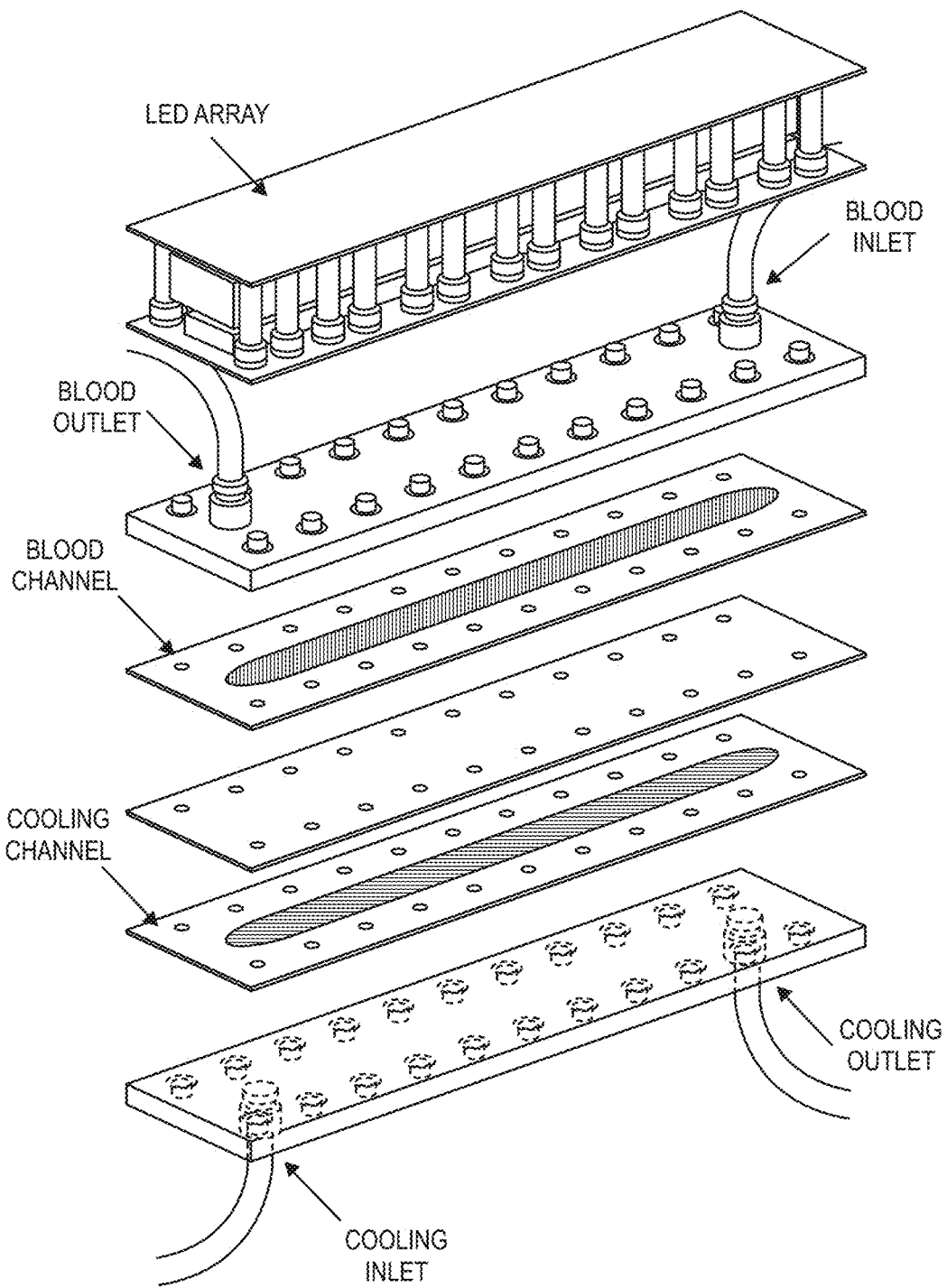
FIG. 6A is an exploded view of microfluidic photoreactor assembly, in accordance with embodiments herein.

To demonstrate the efficacy of the microfluidic photoreactor a prototype was constructed, a mathematical model of bilirubin isomerization was developed and theoretically evaluated for the potential of using the device to treat neonatal jaundice. The prototype device is illustrated in FIG. 6A. The device contains two channels, one for perfusion of blood and the other for perfusion of a cooling fluid, for example water. In the device depicted, blood illumination is provided by an LED array situated on top of the photoreactor housing. Two LED arrays were constructed, one with a peak wavelength of 505 nm and the other with a peak wavelength of 470 nm. These wavelengths were chosen to explore tradeoffs between bilirubin photoconversion and photochemical damage to blood components. Current phototherapy light sources emit at wavelengths ranging between about 400 nm and 520 nm. While absorption of light by bilirubin in blood exhibits a maximum for blue light with a wavelength of about 475 nm, (Lamola A A, Bhutani V K, Wong R J, Stevenson D K, McDonagh A F. The effect of hematocrit on the efficacy of phototherapy for neonatal jaundice. Pediatr. Res. July 2013; 74(1):54-60) there is evidence that photochemical damage is significantly lower for green light than blue light (Sideris E G, Papageorgiou G C, Charalampous S C, Vitsa E M. A spectrum response study on single strand DNA breaks, sister chromatid exchanges, and lethality induced by phototherapy lights. Pediatr. Res. July 1981; 15(7):1019-1023; Roll E B, Christensen T. Formation of photoproducts and cytotoxicity of bilirubin irradiated with turquoise and blue phototherapy light. Acta Paediatr. October 2005; 94(10):1448-1454; Christensen T, Kinn G, Granli T, Amundsen I. Cells, bilirubin and light: formation of bilirubin photoproducts and cellular damage at defined wavelengths. Acta Paediatr. January 1994; 83(1):7-12). LED arrays with peaks at 450 nm and 485 nm will also be constructed and tested, see Example 2.

The prototype device shown in FIG. 6A was used to evaluate conversion of bilirubin to lumirubin for various operating conditions. Pilot trials revealed that, in the absence of a heat exchanger to control the temperature of the blood, excessive heating occurred for high LED power settings. This heating caused substantial lysis of red blood cells. Therefore, all subsequent trials were carried out using a heat exchanger perfused with 20° C. water from a refrigerated water bath. This heat exchanger maintained the blood temperature at the reactor outlet below 37° C., and completely eliminated hemolysis.

Figure 6B:
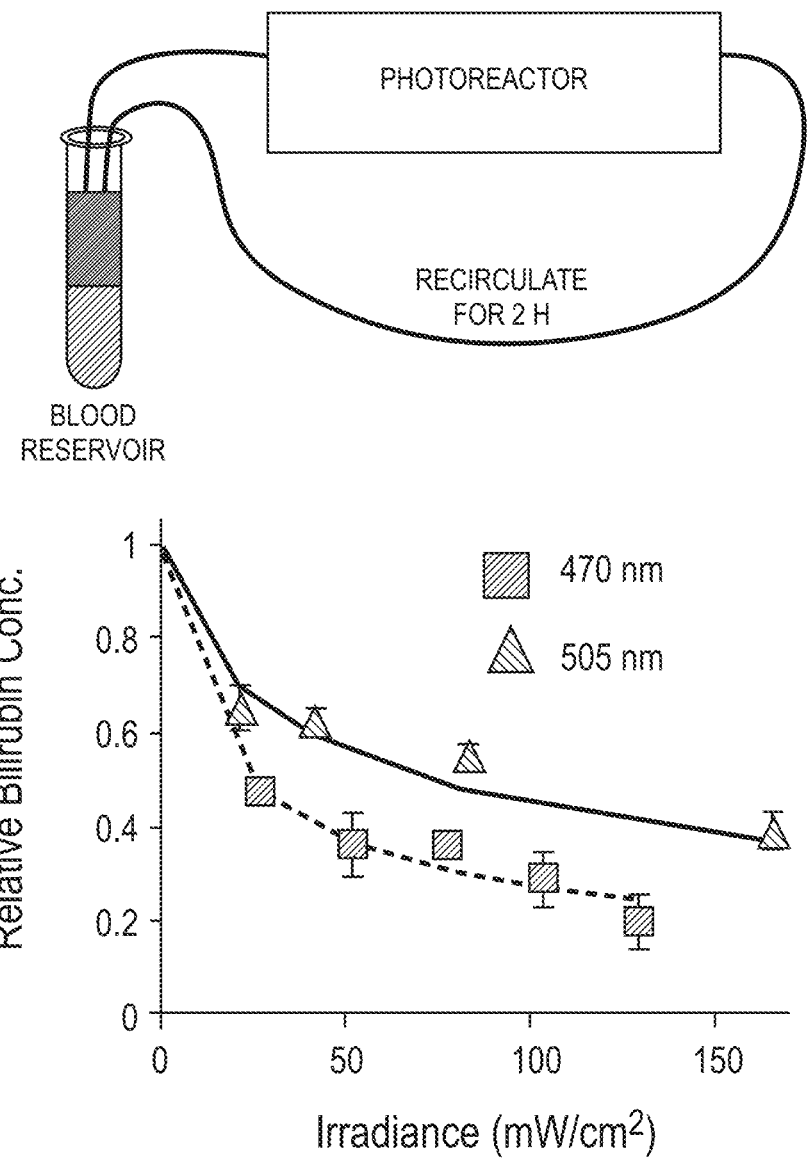
FIG. 6B is a schematic and a graph showing the effect of light intensity and wavelength on bilirubin conversion for a 2 h treatment using a 250 μm thick reactor.

To examine the effects of light intensity on conversion of bilirubin to lumirubin, bilirubin-spiked blood was circulated through the photoreactor under various LED power settings, and the resulting decrease in bilirubin concentration in the reservoir was measured after two hours (FIG. 6B). The bilirubin concentration was estimated using a two point direct spectrophotometric method (Kazmierczak S C, Robertson A F, Catrou P G, Briley K P, Kreamer B L, Gourley G R. Direct spectrophotometric method for measurement of bilirubin in newborns: comparison with HPLC and an automated diazo method. Clin. Chem. July 2002; 48(7):1096-1097; Laterza O F, Smith C H, Wilhite T R, Landt M. Accurate direct spectrophotometric bilirubin measurement combined with blood gas analysis. Clin. Chim. Acta. September 2002; 323(1-2):115-120; Harrison S P, Barlow I M. Three direct spectrophotometric methods for determination of total bilirubin in neonatal and adult serum, adapted to the Technicon RA-1000 analyzer. Clin. Chem. September 1989; 35(9):1980-1986) that accounts for the absorption properties of hemoglobin, bilirubin and lumirubin. As shown in FIG. 6B, the bilirubin concentration decreased as the LED power increased, indicating greater conversion of bilirubin to lumirubin for higher light intensities. Bilirubin concentration decreased to a greater extent for the 470 nm LED array than the 505 nm array. To evaluate the effect of reactor thickness, similar trials were carried out using microchannel heights of 125 µm, 250 µm and 500 µm, while holding the incident light intensity constant. The final bilirubin concentration was lowest for the 125 µm thick channel and highest for the 500 µm thick channel, which is consistent with the expected decrease in bilirubin conversion in the thick channel as a result of light attenuation. In fact, the measured light intensity at the bottom of the 500 µm channel was less than 0.1% of the incident light intensity. The bilirubin concentration data was analyzed using a mathematical model of bilirubin conversion in the photoreactor, resulting in model fits (lines in FIG. 6B) that are in reasonable agreement with the experimental data. The model accounts for light attenuation, diffusion, advection and reaction; the only fitting parameter is the light-intensity-dependent bilirubin isomerization rate constant. The best-fit reaction rate constant is consistent with the published quantum yield for the lumirubin isomerization reaction (McDonagh A F, Agati G, Fusi F, Pratesi R. Quantum yields for laser photocyclization of bilirubin in the presence of human serum albumin. Dependence of quantum yield on excitation wavelength. Photochem. Photobiol. September 1989; 50(3):305-319).

Figure 2:
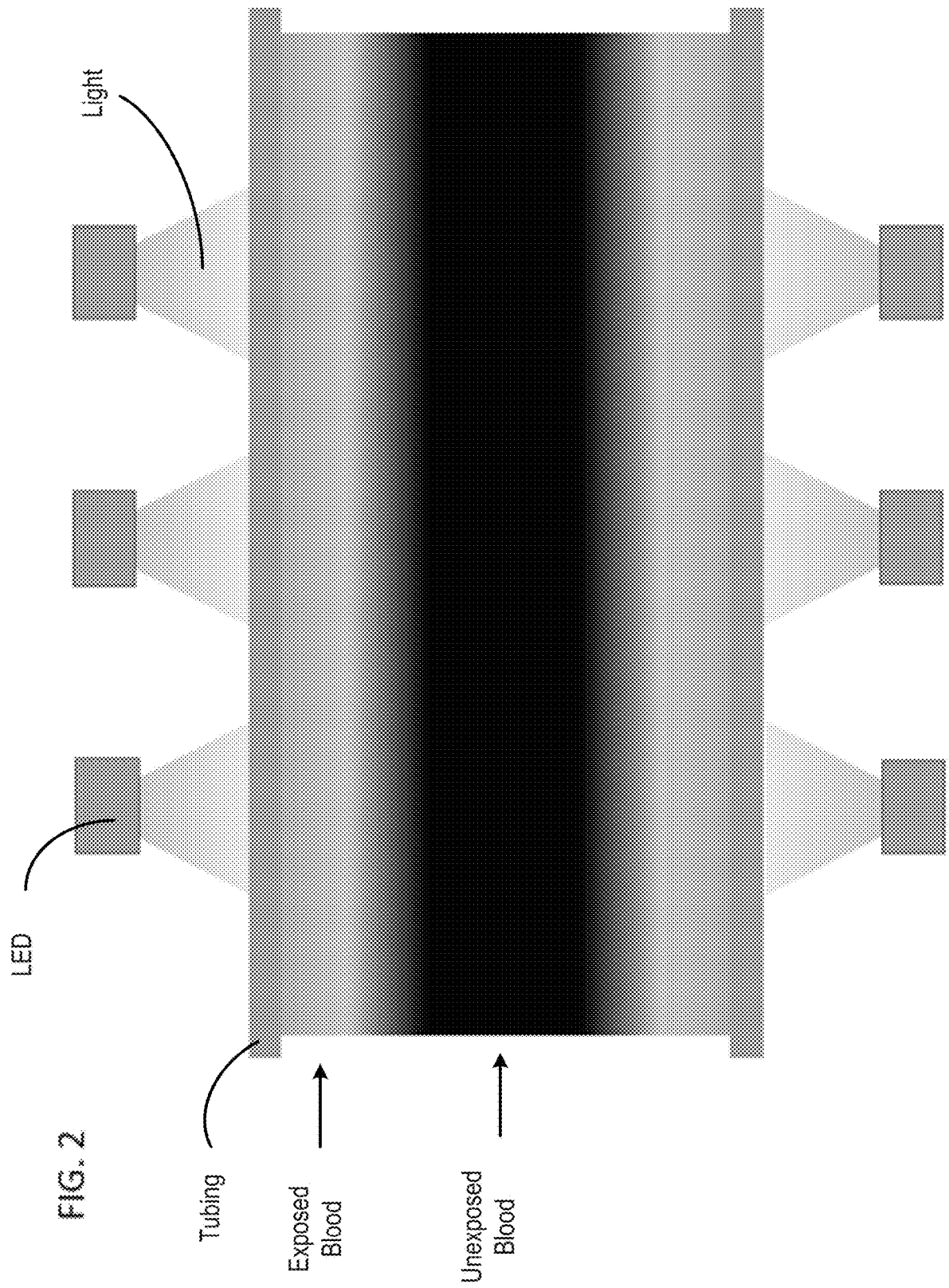
FIG. 2 is a schematic illustrating the problem with using a meso/macrofluidic architecture (e.g. tubing). The dark region due to high light attenuation in blood. The unexposed blood equals added dead volume. In addition, a larger device requires more blood outside the body.
Figure 3:
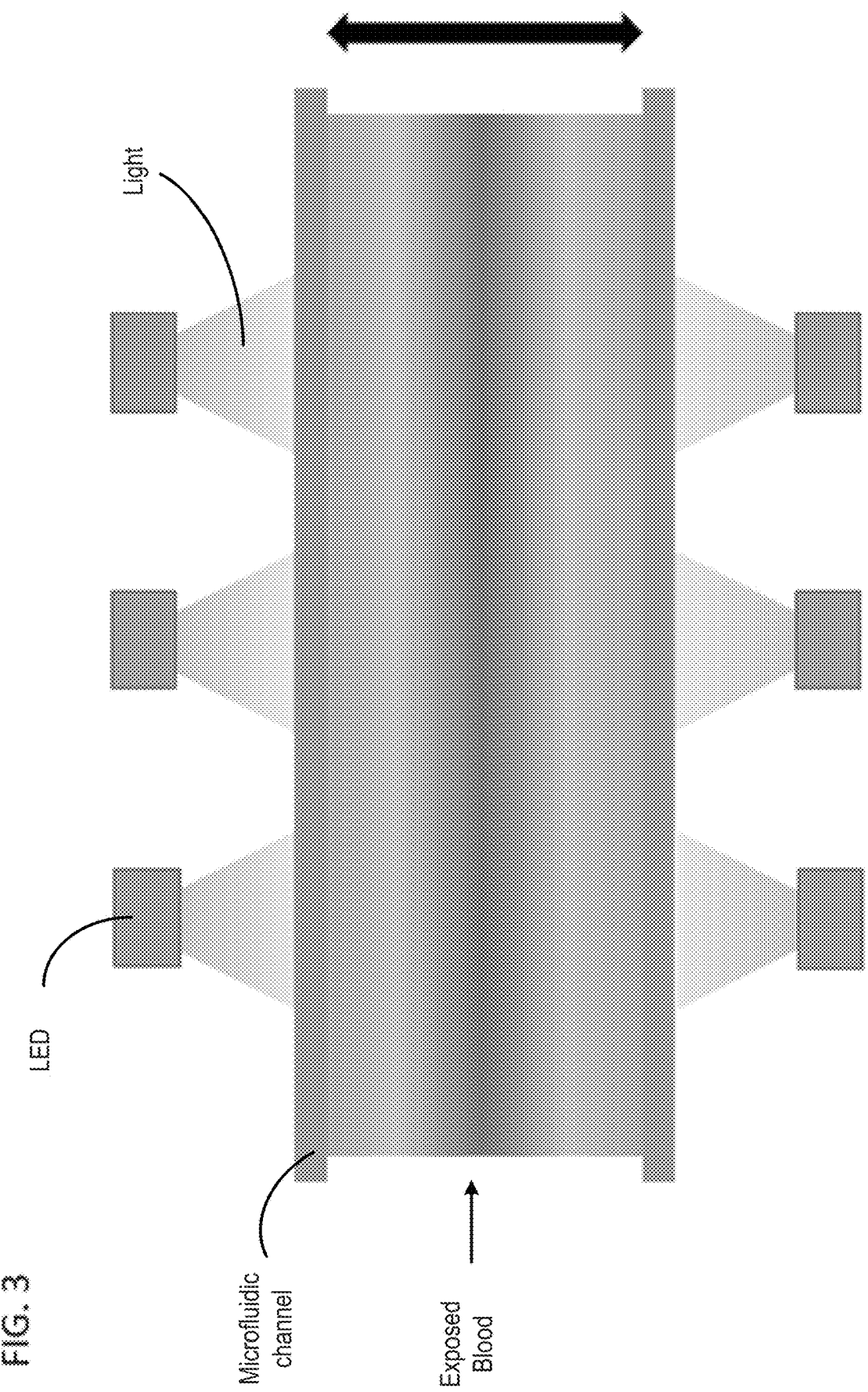
FIG. 3 is a schematic illustrating microfluidic architecture, in accordance with embodiments herein. In a microfluidic environment blood is more evenly exposed. Thus higher device efficiency decreases device volume. In addition, there is near instantaneous heat transfer between the blood and the surrounding microfluidics.
Figure 4:
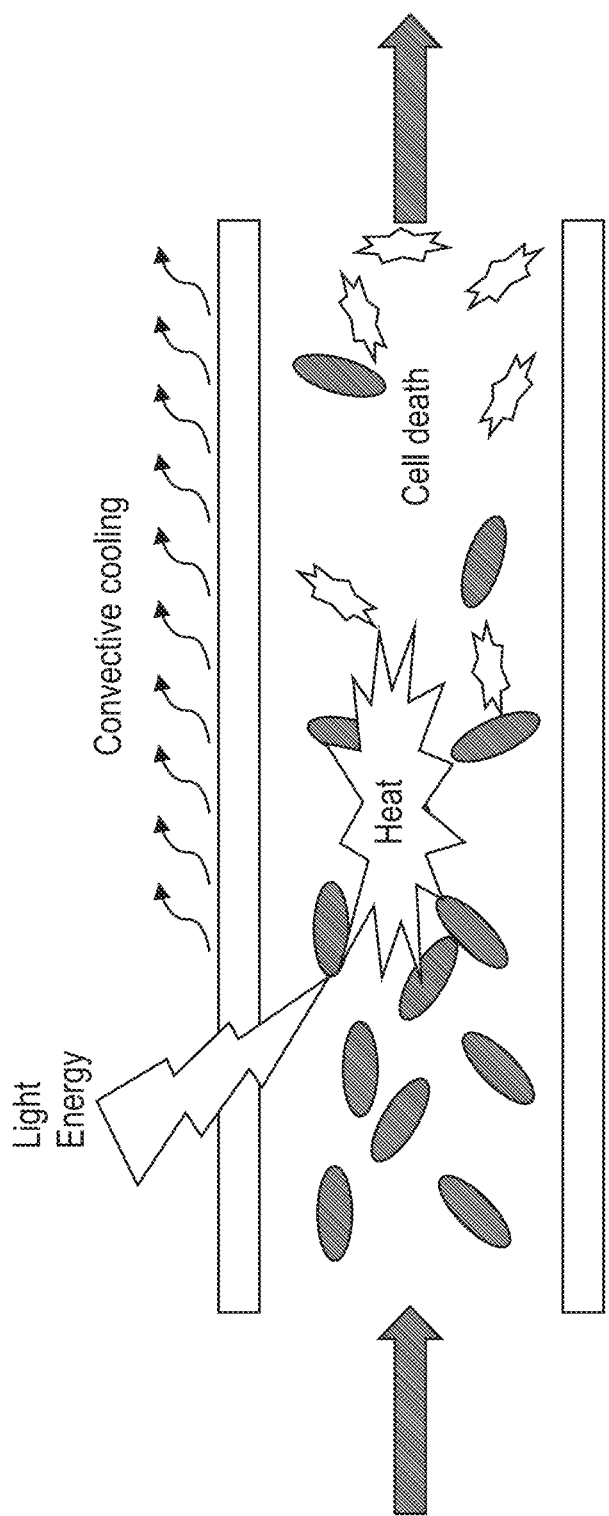
FIG. 4 is a schematic illustrating the effect of passive or air cooling on blood in a microfluidic device. Blue light enters the device. Hemoglobin in red blood cells has high absorbance at this wavelength (~470 nm). The light energy heats the cells from the inside, if not quickly removed the cells die (hemolysis). This heat must be removed quickly, resistance to heat transfer happens within the channel, through the wall material and through a convective cooling boundary. Forced convective cooling (fans) cannot provide the cooling necessary to use higher intensity exposure, limiting the device to exposure power more along the lines of traditional phototherapy
Figure 5:
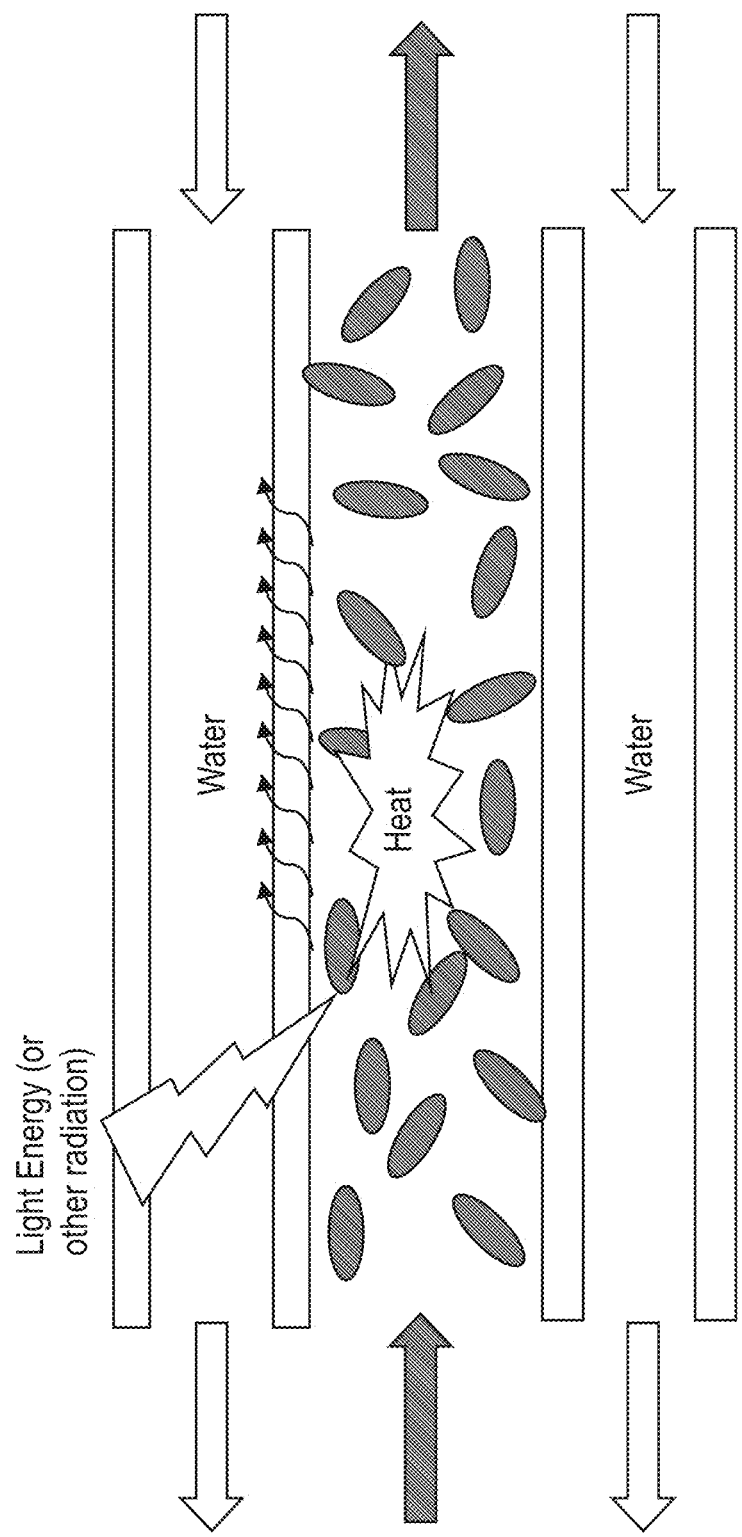
FIG. 5 is a schematic illustrating the effect of active water cooling on blood in a microfluidic device. Countercurrent meso/mico-fluidic heat exchangers are incorporated onto the device. The thin water layer does not impact the light entering the device. Heat generated in the channel is quickly removed preventing the cells from overheating and dying. The microfluidic blood channel is thin enough to have near instantaneous removal, i.e. little to no heat gradient from the inside to the walls.

Specifically, FIG. 2 is a schematic illustrating the problem with using a meso/macrofluidic architecture (e.g. tubing). The dark region due to high light attenuation in blood. The unexposed blood equals added dead volume. In addition, a larger device requires more blood outside the body. By contrast, FIG. 3 is a schematic illustrating microfluidic architecture, in accordance with embodiments herein. In a microfluidic environment blood is more evenly exposed. Thus higher device efficiency decreases device volume. In addition, there is near instantaneous heat transfer between the blood and the surrounding microfluidics.

Figure 6C:
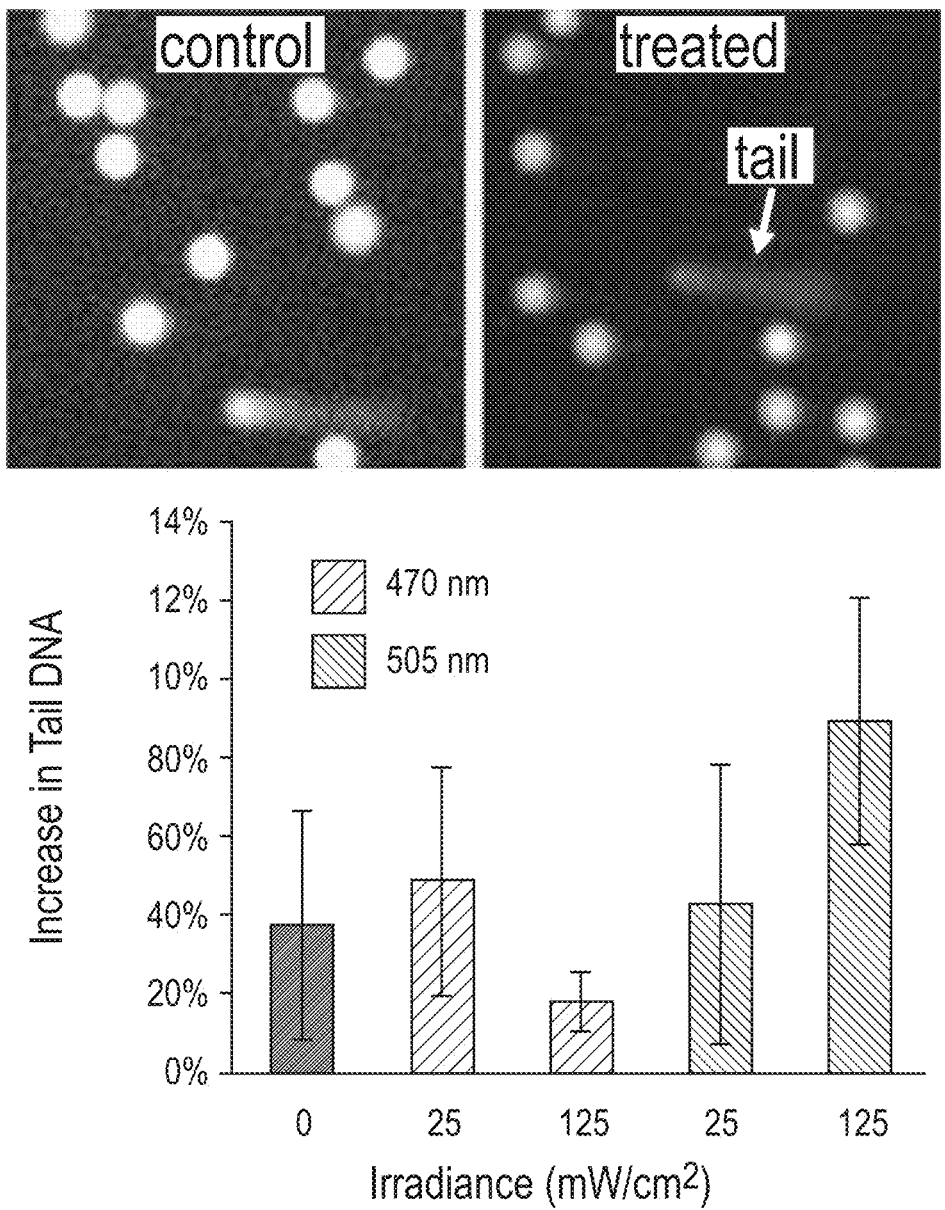
FIG. 6C is a set of digital images and a graph showing the effect of light intensity and wavelength on white blood cell DNA damage.

The potential for photochemical damage to white blood cell DNA was also examined (Aouthmany M M. Phototherapy increases hemoglobin degradation and bilirubin production in preterm infants. J. Perinatol. June 1999; 19(4): 271-274; Aycicek A, Kocyigit A, Erel O, Senturk H. Phototherapy causes DNA damage in peripheral mononuclear leukocytes in term infants. J. Pediatr. (Rio J.). March-April 2008; 84(2):141-146; Cohen A N, Ostrow J D. New concepts in phototherapy: photoisomerization of bilirubin IX alpha and potential toxic effects of light. Pediatrics. April 1980; 65(4):740-750; Howe R B, Hadland C R, Engel R R. Effect of phototherapy on serum bilirubin levels and red blood cell survival in congenitally jaundiced Gunn rats. J. Lab. Clin. Med. August 1978; 92(2):221-227; Karakukcu C, Ustdal M, Ozturk A, Baskol G, Saraymen R. Assessment of DNA damage and plasma catalase activity in healthy term hyperbilirubinemic infants receiving phototherapy. Mutat. Res. November-December 2009; 680(1-2):12-16; Maisels M J, Kring E A. Does intensive phototherapy produce hemolysis in newborns of 35 or more weeks gestation? J. Perinatol. August 2006; 26(8):498-500; Ostrea E M, Jr., Cepeda E E, Fleury C A, Balun J E. Red cell membrane lipid peroxidation and hemolysis secondary to phototherapy. Acta Paediatr. Scand. May 1985; 74(3):378-381; Roll E B, Christensen T, Gederaas O A. Effects of bilirubin and phototherapy on osmotic fragility and haematoporphyrin-induced photohaemolysis of normal erythrocytes and spherocytes. Acta Paediatr. October 2005; 94(10):1443-1447; Sato H, Kashiwamata S, Kuroyanagi M, Yamasaki Y. Effect of phototherapy on erythrocyte membrane proteins of full-term and premature human newborn infants. Acta Paediatr. Scand. 1981; 70(3):409-412; Tozzi E, Tozzi-Ciancarelli M G, Di Giulio A, et al. In vitro and in vivo effects of erythrocyte phototherapy on newborns. Biol. Neonate. 1989; 56(4):204-209; Tozzi-Ciancarelli M G, Amicosante G, Menichelli A, Di Giulio S, Del Principe D. Photodynamic damage induced by bilirubin on human platelets: possible relevance to newborn pathology. Biol. Neonate. 1985; 48(6): 336-340; Yahia S, Shabaan A E, Gouida M, et al. Influence of hyperbilirubinemia and phototherapy on markers of genotoxicity and apoptosis in full-term infants. Eur. J. Pediatr. April 2015; 174(4):459-464; Gathwala G, Sharma S. Oxidative stress, phototherapy and the neonate. Indian J. Pediatr. November 2000; 67(11):805-808). Previous studies show that the total light dose and wavelength are the key factors affecting light-induced cell damage (Sideris E G, Papageorgiou G C, Charalampous S C, Vitsa E M. A spectrum response study on single strand DNA breaks, sister chromatid exchanges, and lethality induced by phototherapy lights. Pediatr. Res. July 1981; 15(7):1019-1023; Roll E B, Christensen T. Formation of photoproducts and cytotoxicity of bilirubin irradiated with turquoise and blue phototherapy light. Acta Paediatr. October 2005; 94(10):1448-1454; Christensen T, Kinn G, Granli T, Amundsen I. Cells, bilirubin and light: formation of bilirubin photoproducts and cellular damage at defined wavelengths. Acta Paediatr. January 1994; 83(1):7-12; Kahveci H, Dogan H, Karaman A, Caner I, Tastekin A, Ikbal M. Phototherapy causes a transient DNA damage in jaundiced newborns. Drug Chem. Toxicol. January 2013; 36(1):88-92; Karadag A, Yesilyurt A, Unal S, et al. A chromosomal-effect study of intensive phototherapy versus conventional phototherapy in newborns with jaundice. Mutat. Res. May 31, 2009; 676(1-2):17-20; Rosenstein B S, Ducore J M. Enhancement by bilirubin of DNA damage induced in human cells exposed to phototherapy light. Pediatr. Res. January 1984; 18(1):3-6; Tatli M M, Minnet C, Kocyigit A, Karadag A. Phototherapy increases DNA damage in lymphocytes of hyperbilirubinemic neonates. Mutat. Res. Jun. 30 2008; 654(1):93-95; Wu F Y, Iijima K, Nishida A, Higurashi M. Sister chromatid exchanges in the peripheral lymphocytes of newborns with Down syndrome after in vitro exposure to blue or green light. Mutat. Res. Apr. 6 1996; 367(4):261-264. Therefore, trials were designed to deliver a light dose comparable to conventional phototherapy, but using higher light intensity over a shorter duration. DNA damage was assessed using the comet assay (Collins A R, Dusinska M, Gedik C M, Stetina R. Oxidative damage to DNA: do we have a reliable biomarker? Environ. Health Perspect. May 1996; 104 Suppl 3:465-469). Briefly, WBCs were isolated, embedded in an agarose gel, lysed and subjected to electrophoresis. As shown in FIG. 6C, damaged DNA migrates away from the nucleus and forms a "tail". The extent of damage was quantified in terms of the percentage of DNA in this tail. The plot in FIG. 6C shows the increase in tail DNA after blood was flowed through the photoreactor, compared with a paired control sample that remained in the blood tube. While flow through the fluidic circuit causes some damage, likely due to the peristaltic pump, exposure to high intensity LED light does not appear to be damaging.

Figure 7:
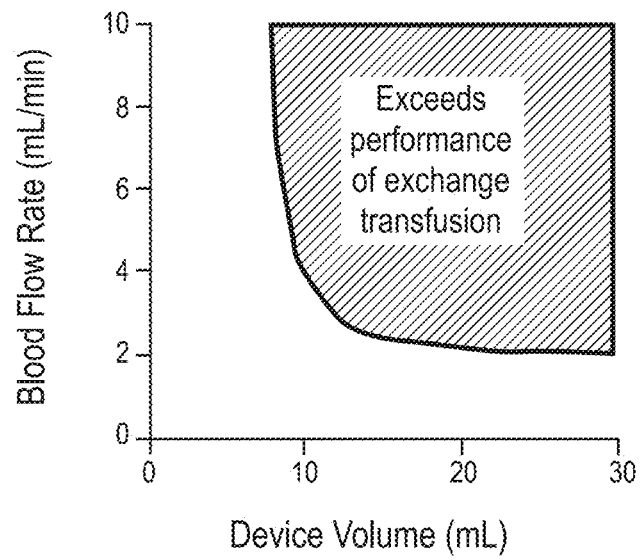
FIG. 7 is graph showing the predicted performance of microfluidic photoreactor for reducing bilirubin levels in a neonate, showing combinations of device volume and flow rate that are expected to exceed the performance of exchange transfusion (LED wavelength=470 nm, reactor height=125 μm; light intensity=130 mW/cm2; neonate blood volume=240 mL).

To evaluate the therapeutic potential of the proposed microfluidic photoreactor, a mathematical model was used to predict the effects of photoreactor treatment on a neonate's bilirubin levels. As shown in FIG. 7, the microfluidic photoreactor is expected to enable efficient blood treatment with a small priming volume and low blood flow rate. In particular, FIG. 7 shows that the microfluidic photoreactor is expected to match the performance of exchange transfusion when the device volume is 10 mL and the blood flow rate is 4 mL/min. A device with such a small volume could be pre-primed with sterile saline, avoiding the need for donor blood. This would not only dramatically improve safety, but also greatly simplify the treatment process. The predictions shown in FIG. 7 also show that the proposed device will meet or exceed the performance of other extracorporeal treatments attempted in the past, but with a much lower blood flow rate and priming volume (Altintas E B, Turkmen D, Karakoc V, Denizli A. Efficient Removal of Bilirubin from Human Serum by Monosize Dye Affinity Beads. J Biomat Sci-Polym E. 2011; 22(7):957-971; Avramescu M E, Sager W F C, Borneman Z, Wessling M. Adsorptive membranes for bilirubin removal. J Chromatogr B. Apr. 25 2004; 803(2):215-223; Scharschmidt B F, Plotz P H, Berk P D, Waggoner J G, Vergalla J. Removing substances from blood by affinity chromatography. II. Removing bilirubin from the blood of jaundiced rats by hemoperfusion over albumin-conjugated agarose beads. J. Clin. Invest. March 1974; 53(3):786-795; Mullon C J P, Tosone C M, Langer R. Simulation of Bilirubin Detoxification in the Newborn Using an Extracorporeal Bilirubin Oxidase Reactor. Pediatr. Res. November 1989; 26(5):452-457; Sideman S, Mor L, Mordohovich D, Mihich M, Zinder O, Brandes J M. Invivo Hemoperfusion Studies of Unconjugated Bilirubin Removal by Ion-Exchange Resin. T Am Soc Art Int Org. 1981; 27:434-438).

Together these results demonstrate two important advantages of microfluidics: (1) thin microchannels reduce light attenuation, enabling more complete illumination of the blood and hence faster reaction kinetics; and (2) thin microchannels facilitate temperature control, making it easier to avoid overheating. The model predictions indicate that the performance of the microfluidic photoreactor is expected to exceed that of the current state of the art phototherapy, as well as exchange transfusion. Importantly, the predictions highlight two advantages of the microfluidic photoreactor that will promote clinical acceptance of the device: (1) the small volume of the device will enable establishment of an extracorporeal circuit without the need for priming with donor blood, and (2) the low blood flow rate will enable safe and convenient vascular access, making it easier for medical practitioners to initiate treatment, and improving the safety of the patient.

Example 2

Exemplary Microfluidic Device

This example describes the development of an exemplary prototype of the device that optimally balances safety and efficacy. This prototype is based on the identified design features for safe and effective photoconversion of bilirubin. In some examples an exemplary microfluidic device is integrated with the surface coating developed in Example 3 and/or used for the animal studies in Example 4.

The working hypothesis is that bilirubin can be rapidly converted to nontoxic photoproducts without light-induced damage to blood cells, while maintaining a low device priming volume and low blood flow rate for improved safety. This hypothesis is tested by performing the following studies.

Quantify the Kinetics of Bilirubin Photoconversion

Trials like those depicted in FIG. 6B are performed to quantify the kinetics of bilirubin photoconversion. Blood is continuously recirculated through the photoreactor and the resulting changes in bilirubin concentration in the blood reservoir is measured. Overall, LED arrays with peak wavelengths of 450 nm, 470 nm, 485 nm and 505 nm, are examined over a range of light intensities. The resulting bilirubin concentration measurements are fit using the photoisomerization model. The predictive ability of the model is evaluated by comparing predictions to experimental data for different reactor thicknesses (125 µm, 250 µm and 500 µm).

Establish Safe Limits for Illumination of Blood with High Intensity LED Light

The preliminary trials as shown in Example 1 demonstrate that light-induced overheating and concomitant hemolysis can be eliminated by integrating a heat exchanger into the photoreactor. However, it is also possible for phototherapy light to cause chemical damage (e.g., oxidation) (Aouthmany M M. Phototherapy increases hemoglobin degradation and bilirubin production in preterm infants. J. Perinatol. June 1999; 19(4):271-274; Aycicek A, Kocyigit A, Erel O, Senturk H. Phototherapy causes DNA damage in peripheral mononuclear leukocytes in term infants. J. Pediatr. (Rio J.). March-April 2008; 84(2):141-146; Cohen A N, Ostrow J D. New concepts in phototherapy: photoisomerization of bilirubin IX alpha and potential toxic effects of light. Pediatrics. April 1980; 65(4):740-750; Howe R B, Hadland C R, Engel R R. Effect of phototherapy on serum bilirubin levels and red blood cell survival in congenitally jaundiced Gunn rats. J. Lab. Clin. Med. August 1978; 92(2):221-227; Karakukcu C, Ustdal M, Ozturk A, Baskol G, Saraymen R. Assessment of DNA damage and plasma catalase activity in healthy term hyperbilirubinemic infants receiving phototherapy. Mutat. Res. November-December 2009; 680(1-2):12-16; Maisels M J, Kring E A. Does intensive phototherapy produce hemolysis in newborns of 35 or more weeks gestation? J. Perinatol. August 2006; 26(8):498-500; Ostrea E M, Jr., Cepeda E E, Fleury C A, Balun J E. Red cell membrane lipid peroxidation and hemolysis secondary to phototherapy. Acta Paediatr. Scand. May 1985; 74(3):378-381; Roll E B, Christensen T, Gederaas O A. Effects of bilirubin and phototherapy on osmotic fragility and haematoporphyrin-induced photohaemolysis of normal erythrocytes and spherocytes. Acta Paediatr. October 2005; 94(10):1443-1447; Sato H, Kashiwamata S, Kuroyanagi M, Yamasaki Y. Effect of phototherapy on erythrocyte membrane proteins of full-term and premature human newborn infants. Acta Paediatr. Scand. 1981; 70(3):409-412; Tozzi E, Tozzi-Ciancarelli M G, Di Giulio A, et al. In vitro and in vivo effects of erythrocyte phototherapy on newborns. Biol. Neonate. 1989; 56(4):204-209; Tozzi-Ciancarelli M G, Amicosante G, Menichelli A, Di Giulio S, Del Principe D. Photodynamic damage induced by bilirubin on human platelets: possible relevance to newborn pathology. Biol. Neonate. 1985; 48(6): 336-340; Yahia S, Shabaan A E, Gouida M, et al. Influence of hyperbilirubinemia and phototherapy on markers of genotoxicity and apoptosis in full-term infants. Eur. J. Pediatr. April 2015; 174(4):459-464; Gathwala G, Sharma S. Oxidative stress, phototherapy and the neonate. Indian J. Pediatr. November 2000; 67(11):805-808). Clinical studies show that phototherapy damages DNA in white blood cells (WBCs), but the damage disappears over time and no long term consequences have been reported (Kahveci H, Dogan H, Karaman A, Caner I, Tastekin A, lkbal M. Phototherapy causes a transient DNA damage in jaundiced newborns. Drug Chem. Toxicol. January 2013; 36(1):88-92). The goal here is to identify illumination conditions for the photoreactor that are as safe as conventional phototherapy. For clinical treatment with the photoreactor it is proposed to use a light intensity about 50-fold higher than conventional phototherapy, but the duration of treatment is much shorter, resulting in a comparable light dose. The available evidence suggests that the extent of DNA damage is proportional to light dose (Sideris E G, Papageorgiou G C, Charalampous S C, Vitsa E M. A spectrum response study on single strand DNA breaks, sister chromatid exchanges, and lethality induced by phototherapy lights. Pediatr. Res. July 1981; 15(7):1019-1023; Karadag A, Yesilyurt A, Unal S, et al. A chromosomal-effect study of intensive phototherapy versus conventional phototherapy in newborns with jaundice. Mutat. Res. May 31, 2009; 676(1-2):17-20; Rosenstein B S, Ducore J M. Enhancement by bilirubin of DNA damage induced in human cells exposed to phototherapy light. Pediatr. Res. January 1984; 18(1):3-6; Wu F Y, Iijima K, Nishida A, Higurashi M. Sister chromatid exchanges in the peripheral lymphocytes of newborns with Down syndrome after in vitro exposure to blue or green light. Mutat. Res. Apr. 6, 1996; 367(4):261-264). In addition, previous studies show that DNA damage decreases as wavelength increases (Sideris E G, Papageorgiou G C, Charalampous S C, Vitsa E M. A spectrum response study on single strand DNA breaks, sister chromatid exchanges, and lethality induced by phototherapy lights. Pediatr. Res. July 1981; 15(7):1019-1023; Roll E B, Christensen T. Formation of photoproducts and cytotoxicity of bilirubin irradiated with turquoise and blue phototherapy light. Acta Paediatr. October 2005; 94(10):1448-1454; Christensen T, Kinn G, Granli T, Amundsen I. Cells, bilirubin and light: formation of bilirubin photoproducts and cellular damage at defined wavelengths. Acta Paediatr. January 1994; 83(1):7-12; Rosenstein B S, Ducore J M. Enhancement by bilirubin of DNA damage induced in human cells exposed to phototherapy light. Pediatr. Res. January 1984; 18(1):3-6). Therefore, the effects of wavelength, light intensity, and exposure time on cell damage will be investigated using experiments similar to those depicted in FIG. 6C. Trials are performed for each of the four LED arrays (450 nm, 470 nm, 485 nm and 505 nm). Specific combinations of light intensity and exposure time are chosen to allow comparison of cell damage for different light intensities at the same total light dose. As a control, trails are performed with the LED lights off. As described under preliminary studies, a modified comet assay will be used to assess DNA damage (Collins A R, Dusinska M, Gedik C M, Stetina R. Oxidative damage to DNA: do we have a reliable biomarker? Environ. Health Perspect. May 1996; 104 Suppl 3:465-469). These trials will allow the identification of the most promising combinations of wavelength and light intensity for effective photoconversion of bilirubin while maintaining acceptable levels of DNA damage. These promising illumination conditions will also be tested for their effects on RBCs. A suite of RBC quality assays is performed after treating blood with the device, including flow cytometry to assess the state of the RBC membrane and hemoglobin oxygen saturation and deformability to give an indication of $O_2$ delivering capacity (Acker J P, Hansen A L, Kurach J D, Turner T R, Croteau I, Jenkins C. A quality monitoring program for red blood cell components: in vitro quality indicators before and after implementation of semiautomated processing. Transfusion. October 2014; 54(10):2534-2543). Overall, these trials will enable the selection of a favorable combination of wavelength and light intensity for use with the prototype device.

Fabricate and Test Microfluidic Photoreactor that Optimally Balances Safety and Efficiency The mathematical model of bilirubin conversion is used to select the incident light intensity, wavelength, reactor geometry and the blood flow rate that best meets the desired device specifications. Based on these predictions a new prototype device is developed at about $\frac{1}{10}^{th}$ of clinical scale; this scale is appropriate for use in the rat studies in Example 4. Whereas the initial prototype was only illuminated from one side using a single LED array (see FIG. 6A), this design is improved upon by including two LED arrays for illumination of the reactor from both sides. This is expected to result in more uniform light intensity throughout the channel height because of the additive effects of the two light intensity profiles. The integrated photoreactor system includes two main components: an LED unit and a reactor unit. The LED unit will contain two LED arrays, one to illuminate the top of the reactor and the other to illuminate the bottom. These LED arrays will be connected to each other and integrated with the power controllers. The reactor unit consists of a blood channel with heat exchanger channels on either side enclosed in an acrylic housing. Based on preliminary predictions, it is expect that only a single reactor channel about 8 cm wide and 15 cm long is needed. The reactor unit will nest between the LED arrays. This modular design is analogous to the expected clinical device, which will comprise a permanent LED unit and a disposable sterile reactor unit. The photoreactor system is tested as follows. To ensure proper function of the LED arrays and to identify the desired power setting, the light output of the LEDs will be quantified using a LI-COR quantum light sensor. Adequate temperature control by running blood through the device and measuring the temperature at the outlet and at the interface between the reactor housing and the LED array. Finally, to test if adequate bilirubin conversion can be achieved in vitro the change in bilirubin concentration after a 4 h (the typical duration of an exchange transfusion) treatment will be measured using a 25 mL blood reservoir.

Based on the data in Example 1, it is expected that the next prototype is demonstrated to be both safe and effective in vitro, paving the way for the animal studies in Example 4. The biggest risk here is that high intensity LED light will cause excessive damage to blood cells. Current phototherapy systems produce a maximum light intensity at the neonate's skin surface that is limited by the potential for skin burns and overheating. Control temperature is much better in the disclosed device is much better system because the microscale reactor geometry enables very efficient heat removal. Thus, it is expected that higher light intensities can be used. The total light dose for photoreactor treatment is only expected to be slightly higher than phototherapy because of the much shorter treatment duration. Because phototherapy is regarded as safe and used on millions of newborns without complications, it is expected that similar light doses can be safely used in our photoreactor. If necessary, the light intensity and deliver a lower light dose. Even a light intensity 5-fold lower than the proposed value is predicted to result in better performance than previously investigated extracorporeal strategies for bilirubin removal (Altintas E B, Turkmen D, Karakoc V, Denizli A. Efficient Removal of Bilirubin from Human Serum by Monosize Dye Affinity Beads. J Biomat Sci-Polym E. 2011; 22(7):957-971; Avramescu M E, Sager W F C, Borneman Z, Wessling M. Adsorptive membranes for bilirubin removal. J Chromatogr B. Apr. 25 2004; 803(2):215-223; Scharschmidt B F, Plotz P H, Berk P D, Waggoner J G, Vergalla J. Removing substances from blood by affinity chromatography. II. Removing bilirubin from the blood of jaundiced rats by hemoperfusion over albumin-conjugated agarose beads. J. Clin. Invest. March 1974; 53(3):786-795; Mullon C J P, Tosone C M, Langer R. Simulation of Bilirubin Detoxification in the Newborn Using an Extracorporeal Bilirubin Oxidase Reactor. Pediatr. Res. November 1989; 26(5):452-457; Sideman S, Mor L, Mordohovich D, Mihich M, Zinder O, Brandes J M. Invivo Hemoperfusion Studies of Unconjugated Bilirubin Removal by Ion-Exchange Resin. T Am Soc Art Int Org. 1981; 27:434-438).

Example 3

Identify Criteria for Surface Modification that Lead to Effective Anticoagulant Function The biocompatibility of the device surface will also be an important design feature. Any artificial surface placed in contact with blood must be treated to prevent protein adsorption and formation of blood clots. It is propose to coat the device with a protein-repellant PEO brush layer decorated with immobilized heparin for localized anticoagulant function. The technology is based on the natural self-assembly of triblock surfactant molecules on polymer surfaces. The surfactants contain a hydrophobic, vinyl-rich polybutadiene (PBD) centerblock, flanked by two hydrophilic PEO chains, which extend into the aqueous environment to form a pendant brush layer on the surface. The adsorbed triblock brush layers can be permanently attached to the polymer surface by a radical chemistry mechanism, which is induced by exposure to y-irradiation or chemical radical sources. Successful covalent immobilization has been demonstrated using y-irradiation, and substantial reduction of adsorption of fibrinogen and other proteins on triblock-coated glass, polycarbonate, silicone, and medical-grade Tygon and polyurethane.[44-47] A significant advantage of the approach, compared to conventional chemical methods used to attach pendant chains, is that y-irradiation is widely used to sterilize medical devices, so coatings could be covalently stabilized "for free" during this process. Anticoagulant activity will be imparted to device surfaces by tethering heparin to the PEO chain ends. We recently demonstrated that unfractionated heparin (UFH), when tethered "end-on" at the ends of pendant PEO chains of triblock surfactants, retains high anticoagulant activity (Fry A K, Schilke K F, McGuire J, Bird K E. Synthesis and anticoagulant activity of heparin immobilized "end-on" to polystyrene microspheres coated with end-group activated polyethylene oxide. J. Biomed. Mater. Res. B Appl. Biomater. July 2010; 94(1):187-195). However, anticoagulant activity was lost when the UFH was tethered with an uncontrolled orientation, highlighting the importance of precisely-targeted conjugation to the tethers (Joshi P, Schilke K F, Fry A, McGuire J, Bird K. Synthesis and evaluation of heparin immobilized "side-on" to polystyrene microspheres coated with end-group activated polyethylene oxide. Int. J. Biol. Macromol. Aug. 1, 2010; 47(2): 98-1). Taken together, these results indicate that one can apply non-fouling and anticoagulant coatings to all of the various parts of the extracorporeal circuit.

The working hypothesis is that controlling the orientation and solvent accessibility of surface-immobilized (tethered) heparin will enable coagulation-free operation of the device without systemic anticoagulants.

Synthesize Surfactant-Based Coatings with Tethered Heparin

It has recently been demonstrated that immobilized heparin is most active when it is tethered in an "end-on" orientation.[48,49] Pyridyldisulfide (PDS) activated PEO-PBD-PEO triblock surfactants from commercial are synthesized from PDS-PEO-OH and bis-hydroxyl-terminated PBD polymers, by the method of Tseng (1995).[51] The triblocks will be self-assembled onto the device, tubing, and connectors from an aqueous solution, and then covalently stabilized by y-irradiation to form a protein-repellent coating (Heintz K, Schilke K F, Snider J, et al. Preparation and evaluation of PEO-coated materials for a microchannel hemodialyzer. Journal of Biomedical Materials Research Part B: Applied Biomaterials. 2014; 102(5):1014-1020; Schilke K F, Snider J L, Jansen L E, McGuire J. Direct imaging of the surface distribution of immobilized cleavable polyethylene oxide-polybutadiene-polyethylene oxide triblock surfactants by atomic force microscopy. Surf Interface Anal. April 2013; 45(4):859-864; Schilke K F, McGuire J. Detection of nisin and fibrinogen adsorption on poly(ethylene oxide) coated polyurethane surfaces by time-of-flight secondary ion mass spectrometry (TOF-SIMS). J. Colloid Interface Sci. Jun. 1 2011; 358(1):14-24). Heparin will be covalently tethered to the pendent PEO chains at their reactive terminal PDS group, providing anticoagulant function.

Whereas in the previous study in Example 1 unfractionated heparin (UFH) was used here use low molecular weight heparin (LMWH) will be used. UFH is a mixture of inactive (70%) and active (30%) forms, and when tethered "end-on" to a surface, UFH retained anti-FXa activity but lost the capacity for inactivation of thrombin (presumably owing to steric hindrance) (Fry A K, Schilke K F, McGuire J, Bird K E. Synthesis and anticoagulant activity of heparin immobilized "end-on" to polystyrene microspheres coated with end-group activated polyethylene oxide. J. Biomed. Mater. Res. B Appl. Biomater. July 2010; 94(1):187-195). LMWH is preferred in clinical practice and has good anti-FXa activity, but lacks activity against thrombin. The bioactive LMWH fraction of UFH will be purified by affinity on an immobilized antithrombin column (Höök M, Björk I, Hopwood J, Lindahl U. Anticoagulant activity of heparin: Separation of high-activity and low-activity heparin species by affinity chromatography on immobilized antithrombin. FEBS Lett. Jul. 1, 1976; 66(1):90-93). The purified LMWH will be modified by aniline-catalyzed reaction of the terminal polysaccharide reducing sugar with a thiol-containing hydrazide (e.g. PDPH and DTT) (Thygesen M B, Munch H, Sauer J, et al. Nucleophilic Catalysis of Carbohydrate Oxime Formation by Anilines. The Journal of Organic Chemistry. 2010, Mar. 5 2010; 75(5):1752-1755; Hermanson G T. Bioconjugate Techniques. 3rd ed: Academic Press; 2013). The resulting heparin thiol group will react with the PDS groups on the ends of the immobilized PEO-PBD-PEO triblocks, tethering the LMWH to the surface in the desired "end-on" orientation (Fry A K, Schilke K F, McGuire J, Bird K E. Synthesis and anticoagulant activity of heparin immobilized "end-on" to polystyrene microspheres coated with end-group activated polyethylene oxide. J. Biomed. Mater. Res. B Appl. Biomater. July 2010; 94(1):187-195). The efficacy of using a heparin conjugated to a coating comprised of polydopamine is also tested.

Characterize the Chemistry and Anticoagulant Function of the Coated Surfaces

Coating quality will be evaluated on model and real materials, by blood protein repulsion at triblock-coated surfaces with and without tethered heparin. With model surfaces, direct detection of adsorption events will be performed using a quartz crystal microbalance with dissipation monitoring (Raman R, Raper M A, Hahn E, Schilke K F. Enhanced capture of bacteria and endotoxin by antimicrobial WLBU2 peptide tethered on polyethylene oxide spacers. Biointerphases. Sep. 20, 2017; 12(5):05G603). With materials actually used in the extracorporeal circuit, the residual enzymatic activity will be measured following contact of triblock-coated surfaces with a B-galactosidase solution. This assay was recently applied to the evaluation of PEO coverage on PDMS, polycarbonate and polyacrylonitrile (Heintz K, Schilke K F, Snider J, et al. Preparation and evaluation of PEO-coated materials for a microchannel hemodialyzer. Journal of Biomedical Materials Research Part B: Applied Biomaterials. 2014; 102(5):1014-1020). Anticoagulant activity of the coatings will be quantified using a standard chromogenic anti-FXa assay kit (Chromogenix COATEST™). Anti-FXa activity will be evaluated by direct application of the COATEST™ assay to suspensions of polystyrene microspheres coated with triblock-tethered heparin (Fry A K, Schilke K F, McGuire J, Bird K E. Synthesis and anticoagulant activity of heparin immobilized "end-on" to polystyrene microspheres coated with end-group activated polyethylene oxide. J. Biomed. Mater. Res. B Appl. Biomater. July 2010; 94(1):187-195). COATEST™ will also be applied to the finer optimization of anti-FXa activity at the surfaces of device and blood-contacting materials (e.g. tubing).

The chemistry of the surface will also be characterize using a suite of high-resolution surface analytical techniques, as described in our previous studies (Schilke K F, McGuire J. Detection of nisin and fibrinogen adsorption on poly(ethylene oxide) coated polyurethane surfaces by time-of-flight secondary ion mass spectrometry (TOF-SIMS). J. Colloid Interface Sci. Jun. 1, 2011; 358(1):14-24; Raman R, Raper M A, Hahn E, Schilke K F. Enhanced capture of bacteria and endotoxin by antimicrobial WLBU2 peptide tethered on polyethylene oxide spacers. Biointerphases. Sep. 20 2017; 12(5):05G603; Baio J E, Schach D, Fuchs A V, et al. Reversible activation of pH-sensitive cell penetrating peptides attached to gold surfaces. Chem. Commun. (Camb.). 2015; 51(2):273-275; Baio J E, Zane A, Jaeger V, et al. Diatom mimics: directing the formation of biosilica nanoparticles by controlled folding of lysine-leucine peptides. J. Am. Chem. Soc. Oct. 29 2014; 136(43):15134-15137; Baio J E, Jaye C, Fischer D A, Weidner T. High-throughput analysis of molecular orientation on surfaces by NEXAFS imaging of curved sample arrays. ACS combinatorial science. Sep. 8, 2014; 16(9):449-453; Baio J E, Weidner T, Ramey D, Pruzinsky L, Castner D G. Probing the orientation of electrostatically immobilized cytochrome C by time of flight secondary ion mass spectrometry and sum frequency generation spectroscopy. Biointerphases. December 2013; 8(1):18; Baio J E, Jaye C, Fischer D A, Weidner T. Multiplexed orientation and structure analysis by imaging near-edge X-ray absorption fine structure (MOSAIX) for combinatorial surface science. Anal. Chem. May 7, 2013; 85(9):4307-4310; Baio J E, Weidner T, Interlandi G, et al. Probing Albumin Adsorption onto Calcium Phosphates by XPS and ToF-SIMS. Journal of vacuum science & technology. B, Microelectronics and nanometer structures: processing, measurement, and phenomena: an official journal of the American Vacuum Society. July 2011; 29(4):4D113; Baio J E, Weidner T, Baugh L, Gamble L J, Stayton P S, Castner D G. Probing the orientation of electrostatically immobilized Protein G B1 by time-of-flight secondary ion spectrometry, sum frequency generation, and near-edge X-ray adsorption fine structure spectroscopy. Langmuir. Jan. 31, 2012; 28(4): 2107-2112). X-ray photoelectron spectroscopy (XPS) will be used to probe the chemical composition of the top ~10 nm of coated device surfaces. The heparin orientation induced by the conjugation scheme will also be assessed with Sum Frequency Generation (SFG) spectroscopy. As a final verification, an in vitro circuit (i.e. the device, a blood reservoir, pump, and tubing) will be operated for 4 hours with anti-coagulant-free blood. Anticoagulant function of the coatings will be evaluated for gross formation of clots and changes in clotting behavior indicated by activated partial thromboplastin time (APTT) assays (Fry A K, Schilke K F, McGuire J, Bird K E. Synthesis and anticoagulant activity of heparin immobilized "end-on" to polystyrene microspheres coated with end-group activated polyethylene oxide. J. Biomed. Mater. Res. B Appl. Biomater. July 2010; 94(1):187-195).

Example 4

Establish the Safety and Efficacy of the Photoreactor Using a Jaundiced Rat Model Examples 2 and 3 demonstrate the safety and efficacy of the photoreactor in vitro and pave the way for in vivo studies using Gunn rats. Gunn rats have a mutation that impairs bilirubin processing and leads to elevated levels of unconjugated bilirubin in the blood (Schreuder A B, Vanikova J, Vitek L, et al. Optimizing exchange transfusion for severe unconjugated hyperbilirubinemia: studies in the Gunn rat. PLoS ONE. 2013; 8(10):e77179; Cuperus F J, Schreuder A B, van Imhoff D E, et al. Beyond plasma bilirubin: the effects of phototherapy and albumin on brain bilirubin levels in Gunn rats. J. Hepatol. January 2013; 58(1):134-140). These rats have previously been used to compare approaches for treatment of hyperbilirubinemia, including exchange transfusion and phototherapy (Schreuder A B, Vanikova J, Vitek L, et al. Optimizing exchange transfusion for severe unconjugated hyperbilirubinemia: studies in the Gunn rat. PLoS ONE. 2013; 8(10):e77179).

Figure 1B:
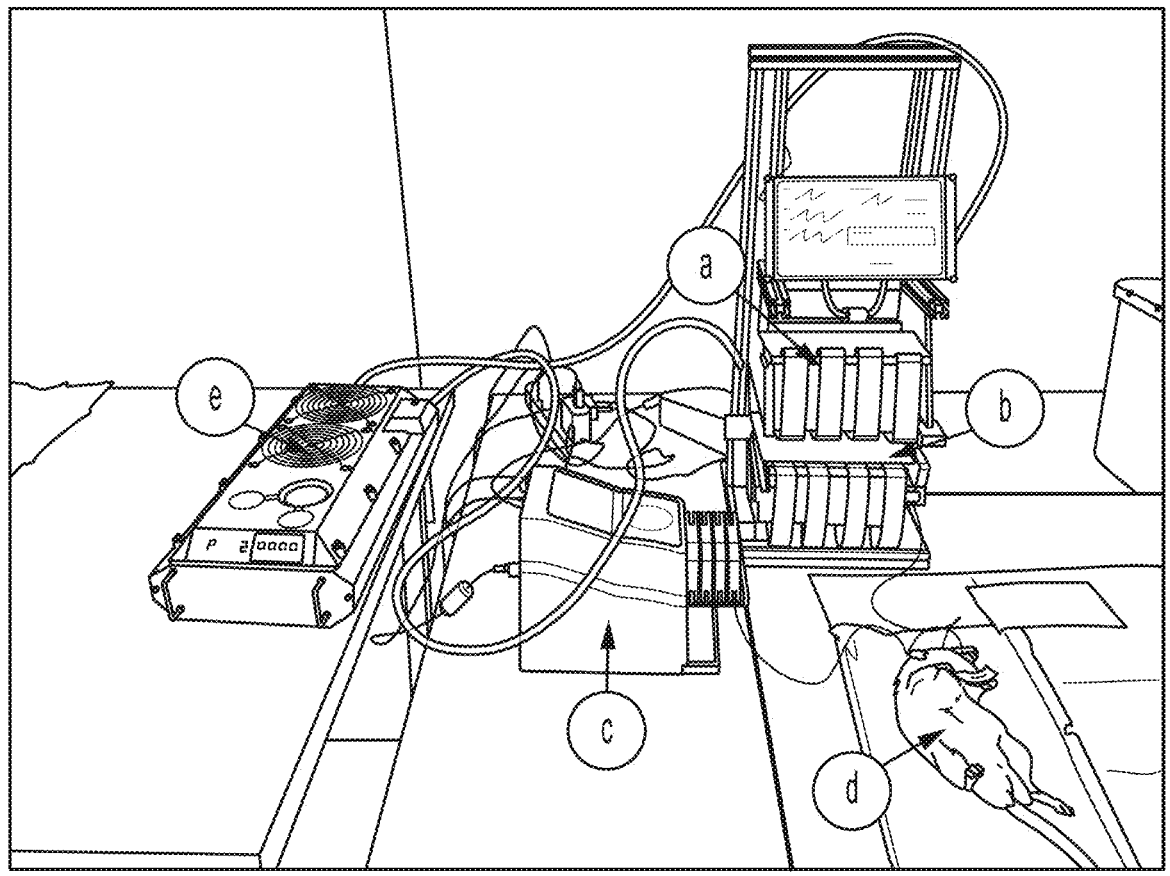

The working hypothesis is that the integrated device will safely reduce bilirubin levels in a Gunn rat model at least as effectively as exchange transfusion, without the need for systemic anticoagulants. As shown in FIGS. 1A-1B, the test platform was scaled up to accommodate the blood volume of a Gunn rat. The exposure device has two panels for illumination of the cartridge from both sides, each with an active exposure area of 15 cm×8 cm, and 512 high power LEDs ($\lambda$=470 nm). In addition to the LED exposure boards, the exposure device components included a touch screen LCD display, 4 power controllers, a power supply, thermocouples, and heatsinks with active cooling fans, all mounted on an extruded aluminum chassis allowing for ease of portability and end user operation.

Figure 8:
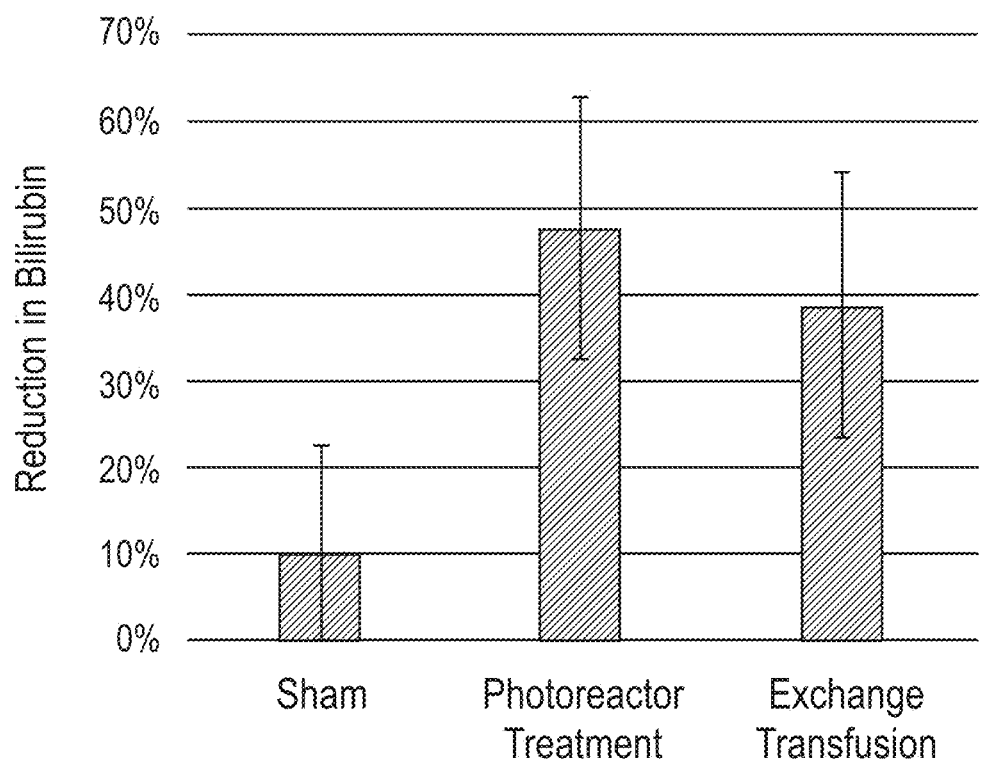
FIG. 8 is a graph of the results of animal study, showing that photoreactor treatment reduces bilirubin levels at least as well as exchange transfusion.

The final results for bilirubin removal are outlined in FIG. 8. Six rats were allocated to each group. The sham treatment experiments were performed first. For this group, 3 of the rats died as a result of issues related to refinement of the experimental method for operating the extracorporeal circuit. The final method involved systemic anticoagulation with heparin and an internal volume of 1.2 mL for the extracorporeal circuit. There were 2 deaths in the exchange transfusion group. All 6 of the rats in the treatment group survived the 4 hour treatment. The percent bilirubin removal for the sham, treatment, and exchange transfusion groups was 10±12%, 48±15%, and 39±15% respectively. These results indicate the reactor had a significant effect on bilirubin removal, and was at least as efficient as exchange transfusion for bilirubin removal. Additionally, these results show the safety of the reactor may surpass that of exchange transfusion due to there being no complications with the treatment group in this study.

Although certain embodiments have been illustrated and described herein, it will be appreciated by those of ordinary skill in the art that a wide variety of alternate and/or equivalent embodiments or implementations calculated to achieve the same purposes may be substituted for the embodiments shown and described without departing from the scope. Those with skill in the art will readily appreciate that embodiments may be implemented in a very wide variety of ways. This application is intended to cover any adaptations or variations of the embodiments discussed herein. Therefore, it is manifestly intended that embodiments be limited only by the claims and the equivalents thereof.

What is claimed is:

1. A microfluidic photoreactor for treating excess bilirubin in blood, the microfluidic photoreactor comprising:
   at least one microfluidic channel module, the at least one microfluidic channel module channel comprising at least one microfluidic channel having: a first end; a second end; a channel height; a channel width; and a channel length, wherein: the first end comprises a sample inlet port and the second end comprises a sample exit port, and wherein the microfluidic channel module is configured to pass blood from the sample inlet port to the sample exit port;
   an illumination module comprising one or more illumination sources disposed about the at least one microfluidic channel module and configured to illuminate blood passing through the at least one microfluidic channel; and
   a heat exchanger module coupled to the at least one microfluidic channel module, wherein the heat exchanger module is configured to extract heat from the at least one microfluidic channel; wherein
   the heat exchanger module comprises a cooling channel having a first end and a second end, and wherein the first end comprises a cooling fluid inlet port and the second end comprises a cooling fluid exit port, and wherein the heat exchanger module is configured to flow cooled liquid.

2. The microfluidic photoreactor of claim 1, wherein the one or more illumination sources comprise a first set of illumination sources configured to illuminate a top side of the at least one microfluidic channel and second set of set illumination sources configured to illuminate a bottom side of the microfluidic channel.

3. The microfluidic photoreactor of claim 1, wherein one or more illumination sources emit light with a wavelength between about 415 nm and about 520 nm.

4. The microfluidic photoreactor of claim 1, wherein one or more illumination sources emit light with a light intensity between about 25 mW/cm2 and about 500 mW/cm2 per side of the at least one microfluidic channel.

5. The microfluidic photoreactor of claim 1, wherein one or more illumination sources comprise LEDs.

6. The microfluidic photoreactor of claim 5, wherein the LEDs comprise LED arrays.

7. The microfluidic photoreactor of claim 1, wherein the height of the at least one microfluidic channel is between about 50 μm and about 500 μm.

8. The microfluidic photoreactor of claim 1, wherein the at least one microfluidic channel has an internal volume and wherein the internal volume is between about 5 mL and about 100 mL.

9. The microfluidic photoreactor of claim 1, wherein the microfluidic photoreactor has a flow rate of between about 1 mL/min and about 200 mL/min.

10. The microfluidic photoreactor of claim 1, wherein the microfluidic channel module comprises a cassette that reversibly couples to the illumination module.

11. The microfluidic photoreactor of claim 10, wherein the cassette further comprises the heat exchanger module.

12. The microfluidic photoreactor of claim 1, wherein the one or more microfluidic channels are preloaded with a biologically compatible fluid.

13. The microfluidic photoreactor of claim 1, wherein the at least one microfluidic channel has a volume between 5 milliliters (mL) and 10 mL.

14. The microfluidic photoreactor of claim 1, wherein the microfluidic channel module is configured to pass blood from the sample inlet port to the sample exit port with a flow rate between 1 milliliter per minute (mL/min) and 10 mL/min.

15. The microfluidic photoreactor of claim 1, wherein the blood includes red blood cells.

16. A system for treating excess bilirubin in blood, comprising:
   at least one microfluidic channel module, the at least one microfluidic channel module comprising at least one microfluidic channel that has: a first end; a second end;

a channel height; a channel width; and a channel length, wherein: the first end comprises a sample inlet port and the second end comprises a sample exit port, and wherein the microfluidic channel module is configured to pass blood from the sample inlet port to the sample exit port;

an illumination module comprising one or more illumination sources disposed about the at least one microfluidic channel module and configured to illuminate blood passing through the at least one microfluidic channel;

a heat exchanger module coupled to the at least one microfluidic channel module, wherein the heat exchanger module is configured to flow cooling fluid through a cooling channel that is thermally coupled with the at least one microfluidic channel to extract heat from the at least one microfluidic channel; and a pump in fluid communication with the at least one microfluidic channel, wherein the pump is configured to pump blood from a subject.

17. The system of claim 16, wherein the pump comprises a peristaltic pump.

18. The system of claim 16, wherein the pump is configured to pump blood at a flow rate of between about 1 mL/min and about 200 mL/min.

19. The system of claim 16, further comprising:

a cooling unit in fluid communication with the heat exchanger module, where the cooling unit is configured to cool the cooling fluid.

20. The system of claim 16, wherein the system is an extracorporeal circuit.

21. A method of treating excess bilirubin in blood, comprising:

passing blood of a subject through at least one microfluidic channel of a microfluidic photoreactor to treat the blood, wherein the microfluidic photoreactor includes:

at least one microfluidic channel module, the at least one microfluidic channel module channel comprising at least one microfluidic channel having: a first end; a second end; a channel height; a channel width; and a channel length, wherein: the first end comprises a sample inlet port and the second end comprises a sample exit port, and wherein the microfluidic channel module is configured to pass blood from the sample inlet port to the sample exit port;

an illumination module comprising one or more illumination sources disposed about the at least one microfluidic channel module and configured to illuminate blood passing through the at least one microfluidic channel; and a heat exchanger module coupled to the at least one microfluidic channel module, wherein the heat exchanger module is configured to flow cooling fluid through a cooling channel that is thermally coupled with the at least one microfluidic channel to extract heat from the at least one microfluidic channel; and returning the treated blood to the subject.

22. The method of claim 21, wherein the subject is selected for treatment as diagnosed with excess bilirubin in the blood.

23. The method of claim 21, wherein the subject is a neonate.

24. The method of claim 21, wherein the subject is an adult.

* * * * *